US011702707B2

(12) United States Patent
Makarov et al.

(10) Patent No.: US 11,702,707 B2
(45) Date of Patent: *Jul. 18, 2023

(54) SYSTEMS AND METHODS FOR ASSESSING CONTAMINATION OF DRINKING WATER

(75) Inventors: Sergei S. Makarov, Morrisville, NC (US); Alexander Vladimirovich Medvedev, Durham, NC (US)

(73) Assignee: ATTAGENE, INC., Morrisville, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 14/343,846

(22) PCT Filed: Sep. 8, 2012

(86) PCT No.: PCT/US2012/054336
§ 371 (c)(1),
(2), (4) Date: Jun. 23, 2014

(87) PCT Pub. No.: WO2013/052237
PCT Pub. Date: Apr. 11, 2013

(65) Prior Publication Data
US 2014/0311907 A1 Oct. 23, 2014

Related U.S. Application Data

(60) Provisional application No. 61/532,122, filed on Sep. 8, 2011.

(51) Int. Cl.
*C12Q 1/6897* (2018.01)
*G01N 21/64* (2006.01)

(52) U.S. Cl.
CPC ....... *C12Q 1/6897* (2013.01); *G01N 21/6486* (2013.01)

(58) Field of Classification Search
CPC ............ C12Q 1/6897; C12Q 2522/101; G01N 33/5014; G01N 33/5041; G01N 2520/00; G01N 33/5005; G01N 33/5008; G01N 33/502; G01N 33/5023; G01N 33/5067; G16B 5/00–5/30; C12N 2502/00–2502/99; C12N 2830/002; C12N 2830/34; C12N 2830/80–2830/85; C40B 30/06; C40B 40/02
See application file for complete search history.

(56) References Cited

U.S. PATENT DOCUMENTS

| | | | | |
|---|---|---|---|---|
| 5,683,868 A | * | 11/1997 | LaRossa | C12N 9/0069 435/252.33 |
| 2003/0108877 A1 | | 6/2003 | Blais et al. | |
| 2005/0053971 A1 | | 3/2005 | Chenchik et al. | |
| 2006/0143718 A1 | | 6/2006 | Nebert | |
| 2006/0160108 A1 | * | 7/2006 | Romanov et al. | 435/6 |
| 2007/0122870 A1 | | 5/2007 | Turley et al. | |
| 2010/0009348 A1 | | 1/2010 | Romanov et al. | |
| 2010/0204924 A1 | * | 8/2010 | Wolfe | C02F 1/008 702/25 |
| 2010/0261219 A1 | | 10/2010 | Kim et al. | |

FOREIGN PATENT DOCUMENTS

| | | | |
|---|---|---|---|
| CN | 2505842 Y | 8/2002 | |
| CN | 101349687 A | 1/2009 | |
| KR | 2000-0031934 A | 6/2000 | |
| WO | WO-9417208 A1 * | 8/1994 | ........... C12Q 1/6897 |
| WO | 2005045426 A2 | 5/2005 | |
| WO | 2006062684 A2 | 6/2006 | |
| WO | 2007038756 A2 | 4/2007 | |
| WO | 2007038757 A2 | 4/2007 | |

OTHER PUBLICATIONS

Agler et al. A high-content glucocorticoid receptor translocation assay for compound mechanism-of-action evaluation. Journal of Biomolecular Screening, vol. 12, No. 8, pp. 1029-1041, 2007.*
Wang et al. Subtracting technique of baselines for capillary electrophoresis signals. Chemical Research in Chinese Universities, vol. 20, No. 2, pp. 134-137, 2004.*
National Primary Drinking Water Regulations, downloaded from https://www.epa.gov/ground-water-and-drinking-water/national-primary-drinking-water-regulations on Apr. 19, 2017 and printed as pp. 1/6-6/6.*
Hirose et al. Revisiona and establishment of Japanese drinking water quality guidelines for di(2-ethylexyl) phthalate, toluene and vinyl chloride—Differences from the latest WHO guidelines drafts. The Journal of Toxicological Sciences, vol. 29, No. 5, pp. 535-539, 2004.*
Saylor et al. What's wrong with the tap? Examining perceptions of tap water and bottled water at Purdue University. Environmental Management, vol. 48, pp. 588-601, 2011, published online Jun. 4, 2011.*
Wu et al. Transcriptional toxicity of the Yangtze River source water on mouse (Mus musculus) detected by cDNA microarray. Exotoxicology, vol. 18, pp. 715-721, 2009. (Year: 2009).*
Romanov et al. Homogeneous reporter system enables quantitative functinal assessment of multiple transcription factors. Nature Methods, vol. 5, No. 3, pp. 253-260, Mar. 2008, including pp. 1/12-12/12 of Supplementary Information. (Year: 2008).*
Tsuneoka et al. c-myc activates RCC1 gene expression through E-box elements. Oncogene, vol. 14, pp. 2301-2311, 1997 (Year: 1997).*
Malloy et al. Interaction of the vitamin D receptor with vitamin D response element in the Mullerian-inhibiting substance (MIS) promoter: Regulation of MIS expression by calcitrol in prostate cancer cells. Endocrinology, vol. 150, No. 4, pp. 1580-1587, Apr. 2009. (Year: 2009).*

(Continued)

*Primary Examiner* — Jennifer Dunston
(74) *Attorney, Agent, or Firm* — Hultquist, PLLC; Steven J. Hultquist

(57) ABSTRACT

A method of determining water quality of a water sample, comprising exposing the water sample to a test cell system; generating at least one profile of ensuing changes in activities of transcription factors in the test cell system in response to such exposing; and determining from the generated at least one profile the water quality of the water sample. Computer systems and kits for carrying out the water quality determination of water specimens are also described, in which water quality can be readily and accurately determined by transcription factor activity analysis.

14 Claims, 27 Drawing Sheets

(56) References Cited

OTHER PUBLICATIONS

Odawara et al. Activation of aromatase expression by retinoic acid receptor-related orphan receptor (ROR) alpha in breast cancer cells. Journal of Biological Chemistry, vol. 284, pp. 17711-17719, Jun. 2009. (Year: 2009).*

Landrier et al. FXRE can function as an LXRE in the promoter of human ileal bile acid-binding protein (I-BABP) gene. FEBS Letters, vol. 553, pp. 299-303, 2003. (Year: 2003).*

Slade et al. Cytokine biomarkers and chronic pain: Association of genes, transcription, and circulating proteins with temporomandibular disorders and widespread palpation tenderness. PAIN, vol. 152, pp. 2802-2812, 2011. (Year: 2011).* http://www.attagene.com/cis-1-list.pdf, downloaded and printed as p. 1/1 on Dec. 26, 2017. (Year: 2017).*

Curtis et al. A portable cell-based impeance sensor for toxicity testing of drinking water. Lab on a Chip, vol. 9, pp. 2176-2183, May 2009. (Year: 2009).*

Van der Meer, Jr., Towards improved biomonitoring tools for an intensified sustainable multi-use environment. Microbial Biotechnology, vol. 9, No. 5, pp. 658-665, 2016. (Year: 2016).*

Rabner et al. Whole cell luminescence biosensor based Lab-On-Chip integrated system for water toxicity analysis. Proceedings of the Society of Photo-Optical Instrumentation Engineers, vol. 6112, 611205, 2006, printed as pp. 1-10. (Year: 2006).*

Vincent et al. Regulation of promoter-CAT stress genes in HepG2 cells by suspensions of particles from ambient air. Fundamental and Applied Toxicology, vol. 39, pp. 18-32, 1997. (Year: 1997).*

Huevel et al. Molecular approaches to identify exposure and risk to specific environmental pollutants. Biomarkers, vol. 4, No. 2, pp. 93-105, 1999. (Year: 1999).*

Tully et al. Effects of arsenic, cadmium, chromium, and lead on gene expression regulated by a battery of 13 different promoters in recombinant HepG2 cells. Toxicology and Applied Pharmacology, vol. 168, pp. 79-90, 2000. (Year: 2000).*

Todd et al. The CAT-Tox(L) Assay: A sensitive and specific measure of stress-induced transcription in transformed human liver cells. Fundamental and Applied Toxicology, vol. 28, pp. 118-128, 1995. (Year: 1995).*

Dohrmann et al. Pax genes and the differentiation of hormone-producing endocrine cells in the pancreas. Mechanisms of Development, vol. 92, pp. 47-54, 2000. (Year: 2000).*

Creusot et al. Evaluation of an hPXR reporter gene assay for the detection of aquatic emerging pollutants: screening of chemicals and application to water samples. Analytical and Bioanalytical Chemistry, vol. 396, No. 2, pp. 569-583, 2010, published online Nov. 29, 2009. (Year: 2009).*

Almuedo-Castillo et al. Dishevelled is essential for neural connectivity and planar cell polarity in planarians. Proceedings of the National Academy of Sciences, USA, vol. 108, No. 7, pp. 2813-2818, Feb. 2011, including pp. 1/11-11/11 of Supporting Information. (Year: 2011).*

Komiya et al. Wnt singal transduction pathways. Organogenesis, vol. 4, No. 2, pp. 68-75, 2008. (Year: 2008).*

Factorial30™ Transcription Reporter System User Manual for Factorial30™ and Factorial30™-XL Kits, www.attagene.com, 2008, pp. 1-34. (Year: 2008).* http://attagene.com/services.php, printed as pp. 1/3-3/3, publicly available on Sep. 26, 2008. (Year: 2008).* http://www.attagene.com/ciendpoint.pdf, printed as pp. 1/2-2/2, publicly available on Jan. 6, 2009. (Year: 2009).*

Louden, M. Data Management and Reporting for Drinking Water Quality Monitoring in Community Managed Supplied. University of Cape Town, pp. 1-172, 2007. (Year: 2007).*

Carleton et al. A relational database for the monitoring and analysis of watershed hydrologic functions I. Database design and pertinent queries. Computers & Geosciences, vol. 31, pp. 393-402, 2005. (Year: 2005).*

Slade, G., et al., "Cytokine biomarkers and chronic pain: association of genes, transcription, and circulating proteins with temporomandibular disorders and widespread palpation tenderness", "Pain", Dec. 2011, pp. 2802-2812, vol. 152.

Van der Linden, S., et al., "Detection of multiple hormonal activities in wastewater effluents and surface water, using a panel of steroid receptor CALUX bioassays", "Environ. Sci. Technol.", Aug. 1, 2008, pp. 5814-5820, vol. 42.

Ashbolt, N., et al., "Indicators of microbial water quality", "Water Quality: Guidelines, Standards and Health", 2001, pp. 289-316, No. Chapter 13, Publisher: IWA Publishing, Published in: London, United Kingdom.

Attagraph Reader Users Manual, www.attagene.com, 2008, pp. 1-27.

Gnatenko, D., et al., "Transcript profiling of human platelets using microarray and serial analysis of gene expression", "Blood", Nov. 14, 2002, pp. 2285-2293, vol. 101.

Hopwood, D., "Fixatives and fixation: a review", "Histochemical Journal", May 1969, pp. 323-360, vol. 1.

Lannan, K., et al., "Breaking the mold: transcription factors in the anucleate platelet and platelet-derived microparticles", "Front Immunol.", Feb. 13, 2015, pp. 1-16, vol. 6, No. 48.

Roodbeen, R., et al., "Synthetic cells and organelles: compartmentalization strategies", "Bioessays", Dec. 2009, pp. 1299-1308, vol. 31.

Pedahzur, R., et al., "Water Toxicity Detection by a Panel of Stress-responsive Luminescent Bacteria", "Journal of Applied Toxicology", 2004, pp. 343-348, vol. 24.

Romanov, S., et al., "Homogeneous reporter system enables quantitative functional assessment of multiple transcription factors", "Nature Methods", Feb. 24, 2008, pp. 253-260, vol. 5, No. 3.

Martin, M.T., et al., "Impact of Environmental Chemicals on Key Transcription Regulators and Correlation to Toxicity End Points within EPA's ToxCast Program", "Chemical Research in Toxicology", Feb. 10, 2010, pp. 578-590, vol. 23, Publisher: American Chemical Society.

* cited by examiner

| RTU NAME | INDUCED BY TRANSCRIPTION FACTORS/PROTOTYPIC | BIOLOGICAL PATHWAYS |
| --- | --- | --- |
| PPRE | PPAR α, δ, γ / ROSIGLITAZONE | NUCLEAR HORMONE RECEPTOR PATHWAY |
| NFI | NF-1 FAMILY | DRUG METABOLISM |
| TGFb | SMAD FAMILY/TGFb | CELL GROWTH AND DIFFERENTIATION TGFb PATHWAY |
| HNF6 | TISSUE SPECIFIC REGULATOR: HNF6 | ENDOCRINE CELL DIFFERENTIATION |
| TCF/β-cat | TCF-1 FAMILY/WNT | CELL ADHESION, WINGLESS-INT PATHWAY |
| Myc | c-Myc, USF1 | CELL CYCLE, PROLIFERATION |
| PXRE | PXR/RIFAMPICIN | NUCLEAR RECEPTOR PATHWAY |
| GRE | GR/DEXAMETHAZONE | DIFFERENTIATION, INFLAMMATION |
| AP-1 | AP-1-LIKE COMPONENTS: C-FOS, C-JUN/PMA | JNK PATHWAY, STRESS RESPONSES |
| ISRE | INTERFERONE REGULATING FACTORS: IRF1, IFR3 INTERFERON | IMMUNE RESPONSES, HOST DEFENSE |
| MRE | MTF-1/HEAVY METALS | HEAVY METALS RESPONSE |
| STAT | STAT FAMILY/IL-6 | JAK PATHWAY |
| NF-kB | REL FAMILY/TNFα, IL-1β, LPS | IMMUNE RESPONSES, IL-1/TOLL RECEPTOR PATHWAY |
| FoxA | FORK HEAD FAMILY: FoxA | HEPATIC SPECIFICATION |
| Xbp1 | X-Box PROTEIN 1 | UNFOLDED PROTEIN RESPONSE, ER STRESS |
| CRE | CREB FAMILY/FORSKOLIN, cAMP | cAMP AND cGMP, NO RECEPTOR, GPCR PATHWAYS |
| AhRE | AhR/DIOXIN, FIC | XENOBIOTIC RESPONSE, HYPOXIA |
| EGR | EGR SUBFAMILY/GROWTH FACTORS | RECEPTOR TYROSINE KINASE PATHWAY |
| ARE | NF-E2 SUBFAMILY: NRF2 | ANTIOXIDATIVE RESPONSES |
| ERE | ER/ESTRAGENS | NUCLEAR HORMONE RECEPTOR PATHWAY |
| Oct | POU DOMAIN FAMILY: OCTs | DEVELOPMENT |
| LXRE | LXRα, b/OXYSTEROLS | NUCLEAR HORMONE RECEPTOR PATHWAY |
| HSE | HSF FAMILY/HEATSHOCK, GELDANAMYCIN | STRESS RESPONSE, HEAT SHOCK |
| SREBP | SREBP SUBFAMILY | LIPID HOMEOSTASIS |
| p53 | p53 FAMILY/DNA DAMAGE | GENOTOXICS STRESS RESPONSES, CHECK POINT CONTROLS |
| BRE | SMAD FAMILY/BMPs | OSTEOBLAST DIFFERENTIATION |
| Pax | Pax FAMILY | DEVELOPMENT OF CNS BETA CELL DIFFERENTIATION |

FIG.4

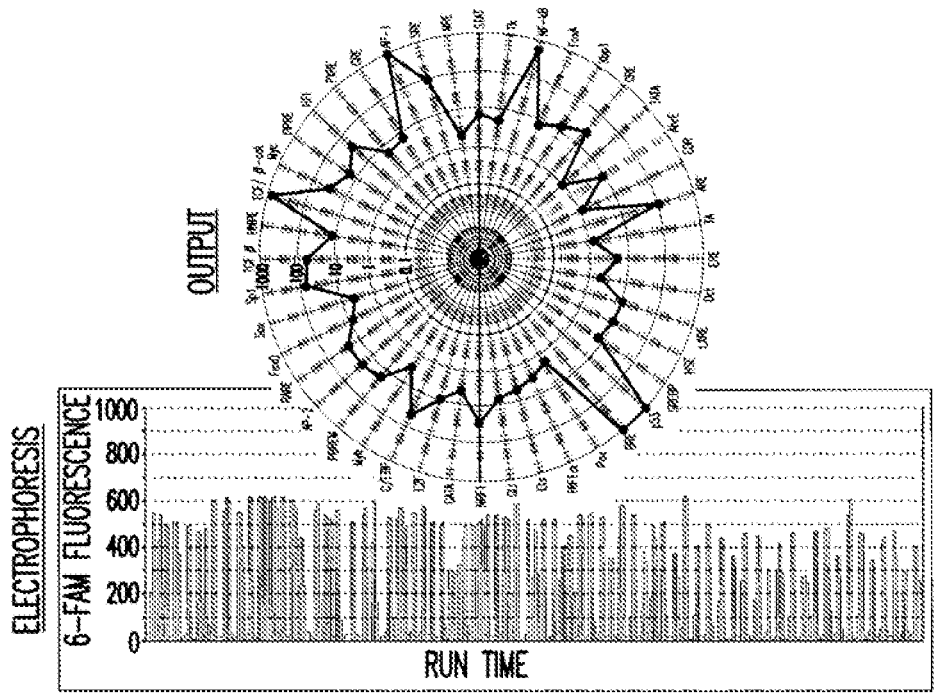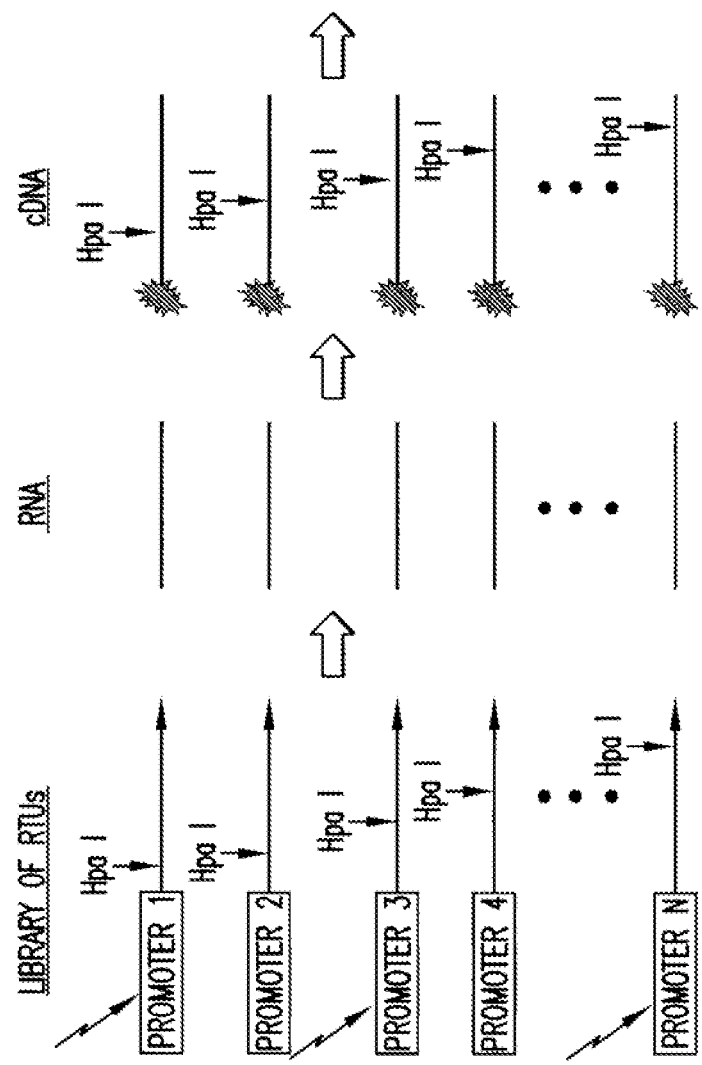
FIG. 6

SYSTEMS AND METHODS FOR ASSESSING CONTAMINATION OF DRINKING WATER

CROSS-REFERENCE TO RELATED APPLICATION

This application is a U.S. national phase under the provisions of 35 U.S.C. § 371 of International Patent Application No. PCT/US12/54336 filed Sep. 8, 2012, which in turn claims the benefit under 35 U.S.C. 119 of U.S. Provisional Patent Application No. 61/532,122 filed Sep. 8, 2011 in the name of Sergei S. Makarov for "SYSTEMS AND METHODS FOR ASSAY OF BIO-CONTAMINANTS IN WATER". The disclosures of such international patent application and priority U.S. provisional patent application are hereby incorporated herein by reference in their respective entireties, for all purposes.

FIELD

The present disclosure relates to water assays and to systems and methods for characterizing water with respect to bio-contaminants therein.

DESCRIPTION OF THE RELATED ART

In recent years, attention has been increasingly focused on water quality for agricultural, industrial and consumer consumption. This has been the result of increasing awareness of the incursion of contaminants into water supplies as a result of the shortcomings of effluent water treatments, e.g., in municipal sewage plants and industrial effluent abatement systems, as well as water conditioning and purification systems in the first instance, to achieve total removal of contaminants from water being processed.

Traditional water treatment for supply of potable water is focused on disinfection of by halogen, aeration, oxygenation or ozonation treatments, but such treatments in many instances are grossly deficient to remove contaminants that pose a health or safety risk to consumers. Likewise, effluent treatment of wastewaters is typically directed to effecting gross reduction of biological oxygen demand (BOD) and/or chemical oxygen demand (COD) and may likewise be highly inadequate in achieving removal of contaminants that pose risks from a health and safety perspective.

These concerns have been fueled by well-publicized instances of pollution and fouling of water supplies in recent years, relating to agricultural pesticide, herbicide and animal waste incursions into watercourses and groundwater, increases in levels of cosmetic components, contraceptive ingredients, heavy metals and myriad other contaminants deriving from water recycling and reuse, increasing acidification of municipal water supplies as a result of corresponding deteriorations in air quality and entry of carbon oxides, sulfites, nitrates and other airborne contaminants into water supplies from the ambient atmosphere, and the threat posed to water quality by increasing industrialization and large-scale farming operations.

Current water safety control systems are based on lists of hazardous substances (e.g., bacterial products, chemical toxins, pesticides, cancerogenes, mutagens, heavy metals, endocrine disruptors, etc.) that are commonly found in drinking water. The maximal tolerable concentrations for these hazardous contaminants are then established and approved by legislative or regulatory authorities. Subsequently, the concentrations of the listed hazardous contaminants in water samples are analyzed by using analytical methods (e.g., using physico-chemical detectors, analytical chemistry, biochemical tests, etc.), and drinking water then is considered safe if concentrations of all evaluated toxicants are within permissible levels.

Such current water safety control systems, however, are insufficient in a number of respects. Each year, thousands of new chemical and biological compounds with unknown toxic properties, such as pesticides, industrial chemicals, and emergent pathogens, enter the environment. The current water control safety systems are focused on a limited number of known threats, but leave thousands of others unaccounted for in assessing the safety and potability of water. The incursion of new chemical and biological contaminants also holds the threat of interactions and reactions that may cause innocuous substances to combine and produce toxic effects that cannot be predicted by current analytical methods.

This poses a dilemma. Of the myriad contaminants extent in water worldwide, only a small number of chemical and biological hazards can be monitored. Current regulatory and enforcement schemes therefore are focused on only the most dangerous threats, viz., those contaminants frequently found in drinking water in harmful concentrations. These current regulatory safety efforts do not address known but non-monitored contaminants. These include spurious toxic substances that are unlikely to be found in drinking water in hazardous concentrations. The risks associated with these substances are acknowledged, but such substances are not monitored.

In addition to the foregoing threats, the thousands of new chemical and biological compounds with unknown toxic properties annually entering the environment and ultimately the water supply represent the most serious contaminant threat.

In addition to the foregoing, the shortcomings of current water safety systems increase the risk of stealthy terrorist attack on national water supplies. Water safety thus has a strong national security component.

As shown by the foregoing, compliance with the current standards does not guarantee or provide a reliable basis for concluding that drinking water is safe.

The foregoing considerations reflect a continuing need for improved testing and assessment technologies that enable water to be characterized as to its purity, safety and biological impact on humans and other animals and organisms, in a ready, reproducible and accurate manner.

SUMMARY

The present disclosure relates to characterization of water, and more specifically to systems, methods and kits for assessing the presence and biological effects of contaminants in water for consumption by humans and other animals and organisms.

The disclosure in one aspect relates to a method of determining water quality of a water sample, comprising:
exposing the water sample to a test cell system so that the test cell system responds to the water sample by change in transcription factor activity in said test cell system;
generating from the test cell system response an output correlative to the change of transcription factor activity in said test cell system; and
determining from comparison of said output with a transcription factor activity reference standard the quality of the water sample.

In another aspect, the invention relates to a method of determining water quality of a water specimen, comprising quantifying impact of contaminants in said water specimen on activities of multiple transcription factors in a test cell system.

In a further aspect, the invention relates to a method of determining relative quality of different water samples, comprising:

exposing each different water sample to a corresponding biosensor comprising multiple transcription factors, wherein the corresponding biosensor is adapted to manifest a transcription factor signature in response to the exposure; and comparing transcription factor signatures of the corresponding biosensors, or of their expression products, to determine relative water quality of the different water samples in relation to one another.

In another aspect, the present invention relates to a method of determining water quality of a water sample, comprising:

introducing into a test cell system comprising a multiplicity of transcription factors, a plurality of reporter constructs whose promoters are regulated by the transcription factors;

exposing the test cell system to the water sample to induce corresponding changes in activities of said multiplicity of transcription factors; and determining water quality of the water sample from a plurality of reporter transcripts produced by the reporter constructs and/or a plurality of reporter proteins produced by the reporter constructs in response to the changes in activities of said multiplicity of transcription factors upon exposing the test cell system to the water sample.

Another aspect of the disclosure relates to a kit for carrying out water quality determination of a water sample, comprising transcription factor signatures for reference library water standards in a graphical format, for visual determinations of relatedness of a transcription factor signature to reference library signatures, to thereby determine water quality of the water sample.

A further aspect of the disclosure relates to a kit for carrying out determinations of water quality of water samples, comprising biosensors, contacting containers in which cells may be contacted with water samples for evaluation, and instructional documents containing protocols for conducting the contacting operation and the further processing of the contacted cell samples for analysis of transcription factor signatures.

Yet another aspect of the disclosure relates to a water quality monitoring system, including a central facility including a relational database operatively coupled with a server communicationally connected to one or more remote facilities, wherein said one or more remote facilities are arranged for collection and processing of local water samples to generate transcription factor activity profiles therefore, and to transmit same to the server, wherein the relational database contains transcription factor activity profiles of reference standards accessible by the server, and wherein the server is configured to determine from local water sample transcription factor activity profiles transmitted to it, in relation to transcription factor activity profile(s) of reference standards accessed from the relational database, the water quality of the local water samples.

Other aspects, features and embodiments of the invention will be more fully apparent from the ensuing disclosure and appended claims.

BRIEF DESCRIPTION OF THE DRAWINGS

FIG. 4 shows a tabulation listing of identified reporter transcription units, the corresponding induction transcription factors, and associated biological pathways.

FIG. 6 is a simplified schematic diagram of the process described in connection with FIG. 5.

DETAILED DESCRIPTION

Figure 1:
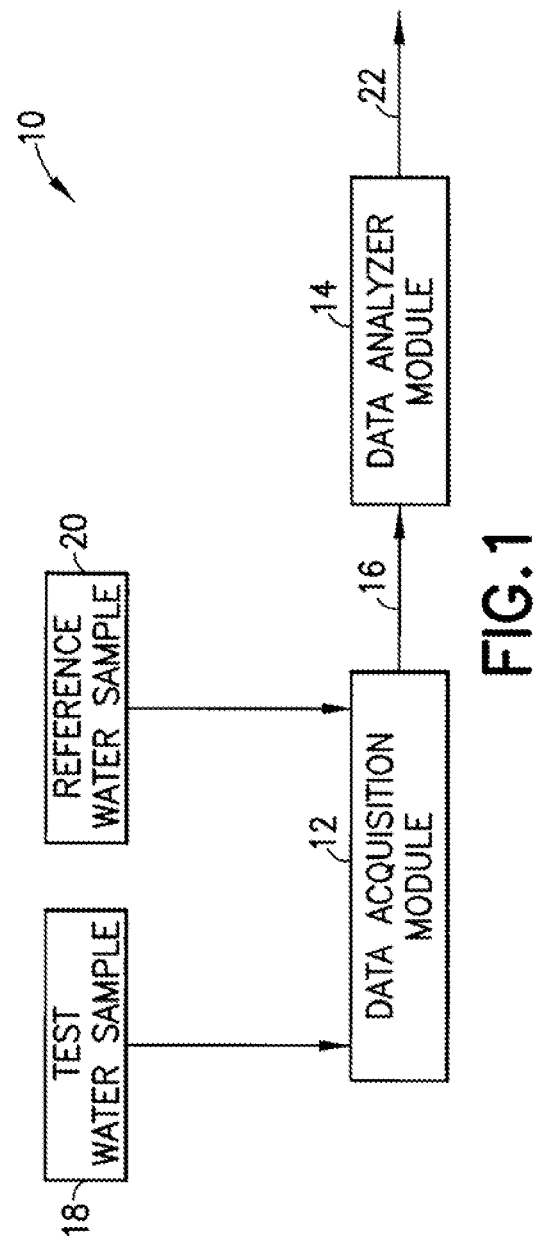
FIG. 1 is a schematic representation of an illustrative water sample assessment system 10, according to one embodiment of the present disclosure.

The present disclosure relates to systems and methods for characterizing and qualifying water, based on the use of cell-based biosensors.

The biological systems utilized for characterization of water in accordance with the present disclosure comprise biosensors. Such biosensors comprise cells, which may be present in a variety of forms, including, without limitation, individual cells, cell cultures, single-cell organisms, microbial populations, multicellular organisms, biological specimens taken or derived from such organisms, such as organs, tissue samples, and tissue cultures. The cells may be endogenous cells, exogenously modified cells, or synthetic cells. The cells can be of any suitable types, and can include human cells, animal cells (such as swine cells, rodent cells, canine cells, bovine cells, ovine cells and/or equestrian cells) cloned cells, plant cells, or the like. The cells may be blood cells, cultured cells, biopsied cells, or cells that are fixed with a preservative or bound to a substrate. The cells can be nucleated, such as white blood cells or suspended endothelial cells, or non-nucleated, such as platelets or red blood cells.

As used herein, the singular forms "a", "an" and "the" are intended to include the plural forms as well, unless the context clearly indicates otherwise.

The various elements, features, aspects, implementations, and embodiments described herein are intended to be non-limitingly construed, and the disclosure therefore is to be understood and interpreted, as encompassing all potential permutations and combinations of such elements, features, aspects, implementations, and embodiments, or a selected one or ones thereof with other elements, features, aspects, implementations, and embodiments, as being within the scope of the disclosure.

The present disclosure enables the assessment of water in a simple, effective and reproducible manner. The disclosure is based on the discovery that in response to hazardous agents, cells activate stress-response pathways that initiate defensive gene expression programs, and such cellular response can be utilized to characterize water in a highly effective manner. The disclosure reflects the fact that different hazards produce distinct stress responses, e.g., inflammatory, metabolic, heat-shock, genotoxic, oxidant stresses, etc. As a result of such distinctive stress responses, the spectrum of stress responses is a signature of a specific hazardous agent when cells are exposed to such agent.

The disclosure thereby is based on a simple premise, that by observing the cellular reaction to sampled water, one can determine if the water is safe to drink, by the criterion that safe water in the assay of the present disclosure produces a minimum of stress responses. The methods and systems of the present disclosure rely on cellular assays that provide effective surveys of the multiple cellular response pathways.

The present disclosure enables the assessment of the quality of a specific water sample, and comparison of its impact on gene regulatory pathways in a test cell system, in which the test cell system is exposed to the water sample to be evaluated, and the profiles of ensuing changes in stress responses of the cell are analyzed to determine the presence or absence of contaminants and the overall quality of water in relation to an analytical standard or specific stress response profile correlative to water of a clean and safe character.

The present disclosure contemplates various specific implementations, in which the change in activities of multiple transcription factors is analyzed by introducing into a test cell system a plurality of reporter constructs whose promotors are regulated by the transcription factors, and the activities of reporter constructs are assessed by analyzing a plurality of reporter transcripts produced by the reporter constructs and/or a plurality of reporter proteins produced by the reporter constructs.

Alternatively, changes of activities of transcription factors can be analyzed by assessing changes in DNA-binding activities in cell extracts, e.g., by using a gel-shift assay.

As a still further alternative, the changes in transcription factor activities can be assessed by analyzing changes in cellular localization of transcription factors (e.g., nuclear translocation of transcription factors) or any other parameters that are associated with transcription factor activities.

The test cell system can be substantially varied in the practice of the present disclosure. For example, the test cell system can comprise an in vitro culture of primary cells or transformed cells or the test cell system can comprise a mixture of different cell types. The test cell system in other embodiments can be or comprise an in vitro organ culture, e.g., a tissue slice culture. In still other implementations, the test cell system can be or comprise organs or tissues of live animals.

In various embodiments, the transcription factor profile can comprise from 2 to 100 transcription factor activities, with lower limits and narrower ranges being useful in specific applications, e.g., from 2 to 50 transcription factor activities, from 2 to 40 transcription factor activities, from 2 to 20 transcription factor activities, or from 2 to 10 50 transcription factor activities.

In algorithmic representations, the transcription factor activity profiles can be represented by vectors with coordinates $x1, x2 \ldots xN$, where $xi$ is the activity of the $i^{th}$ transcription factor, $TF_i$. Comparison of transcription factor profiles can then be carried out by different techniques, e.g., by analyzing correlation of transcription factor profiles, as previously described, or by assessing the Euclidian distance between the transcription factor activity vectors.

Biosensors in the practice of the systems and methods of the present disclosure are utilized to interact with water compositions in a manner eliciting a biological response of the biosensor involving transcription factor activity in the cell(s) of the biosensor. The biosensor cells in the methods of the disclosure undergo transformation in response to the compositions with which the cells interact, so that the cells manifest altered transcription factor activity relative to activity in the cell prior to the interaction with the water composition of interest. By use of a same biosensor, e.g., respective aliquots of a homogeneous cell population, transcription factor activity profiles (referred to herein as "transcription factor signatures") attributable to interaction of different water compositions with the same biosensor can be compared by any of various suitable comparative techniques to determine water quality.

Although the systems and methods described herein are primarily directed to assay of water for presence of contaminants therein, it will be recognized that the general approaches, systems and methodologies of the present disclosure are likewise applicable to food characterization, including liquid nutritional compositions, and foodstuffs of widely varied character.

In order to evaluate water quality in accordance with the present disclosure, multiple stress response pathways of the test cell system is evaluated by biosensors incorporating the transcription factor reporter system, from which reporter signatures are detected, e.g., for an unknown water sample, and a pure water standard sample, to quantitate the nature and extent of stress responses by the test cell system in each instance, to determine whether a sufficiently weak stress response is present to indicate the tested water sample to be safe, or that the test water sample contrariwise induces a strong stress response in the test cell system indicative of an unsafe character of the tested water sample.

For such purpose, a transcription factor signature is generated for each of the unknown water sample and a reference standard water sample. The transcription factor signature can be rendered in any suitable form, including algorithmic, data, and/or graphical forms, as requisite for subsequent analytical comparison, and reporting or other responsive output, using computer(s) and/or networked computer systems that are specially adapted for data acquisition and data processing. Methods of the types described in U.S. Pat. No. 7,771,660 and in U.S. Patent Application Publication 2010009348, and corresponding assays commercially available from Attagene, Inc. (Research Triangle Park, N.C.) under the trademark FACTORIAL can be employed to generate transcription factor signatures in the practice of the present disclosure.

In a specific implementation, the transcription factor signature is generated by constructing a library of reporter transcription units (RTUs), in which each RTU is constructed to include a common plasmid backbone and a unique transcription factor-inducible promoter that is fused to a transcribed reporter sequence. When co-introduced into a cell of interest, e.g., a HepG2 cell, the RTUs produce reporter RNAs in amounts that are commensurate with the activities of the corresponding transcription factors present in the cell. In order to provide equal detection opportunities for different transcription factors, all RTUs are supplied with essentially identical reporter sequences. To distinguish reporter sequences produced by different RTUs, each sequence is provided with a short processing tag, e.g., a Hpal restriction cleavage site, the position which varies among the RTUs.

By such arrangement, reporter sequences can be discriminated upon cleavage with a corresponding processing enzyme. The cleaved reporter species subsequent to such enzymatic processing are separated by high resolution capillary electrophoresis (sequencing) and quantified. All operational steps of this assay protocol can be performed using a homogeneous set of reagents in a single reaction tube, thereby providing highly uniform conditions for detecting multiple transcription factors.

Multiplexed detection of transcription factors can be carried out by introducing the transcription factor reporter library into cells of interest using standard transfection techniques. After transfection, total cellular RNA is isolated and submitted to reverse transcription. Reporter cDNAs are amplified by polymerase chain reaction (PCR) using a pair of primers that is common for all reporters. PCR products then are labeled with fluorescent dye and digested by the Hpal restriction enzyme, producing a distribution of fluorescently labeled DNA fragments of different lengths that are resolved by capillary electrophoresis (CE) and detected as separate fluorescent peaks.

The capillary electrophoresis data can be processed in any suitable manner to provide an output fluorescence spectrum of reporter peaks that is amenable to further analysis and output using standard spreadsheet computer programs. In one embodiment, the capillary electrophoresis data are processed using Attagraph™ CE processing software (Attagene, Inc., Research Triangle Park, N.C.), to algorithmically subtract background fluorescence and enable precise sizing of reporter peaks and noise/reporter peak discrimination. Fluorescence values of individual peaks may be normalized to the sum of signals of all peaks, to generate standardized data. The resulting relative fluorescence values of the individual reporter peaks, and corresponding RTU activity values, as transcription factor signatures, can then be exported into Microsoft Office® Excel® or other spreadsheet for further analysis, e.g., quantitative comparison of respective transcription factor signatures, to assess the quality of an unknown water sample against a reference standard sample.

In addition to the foregoing illustrative technique, as a methodology enabling the concurrent assessment of activities of many dozens of transcription factors to obtain a transcription factor signature, alternative methods may employ profiling of transcription factors in a panel of multiple parallel reporter cell lines. In general, the number of transcription factors employed to provide the transcription factor signature may be varied, as necessary or desirable for a specific cell or cell line to generate a signature that is sufficient for reliably assessing water quality. Thus, in some instances, the transcription factor signature may be based on the profiling of 50 transcription factors, while in other instances, 5-10 transcription factors may be sufficient. It will therefore be recognized that the number and type of transcription factors may be substantially varied in the broad practice of the present disclosure, from a single transcription factor to 50 or more transcription factors.

The generalized method of the present disclosure can be practiced to assess water quality of an unknown water sample in a simple and reproducible manner, by obtaining a transcription factor signature of the unknown water sample in test cells and obtaining a transcription factor signature of a reference water standard in the same (type) test cells, following which the respective transcription factor signatures can be compared utilizing any appropriate algorithms in a computer-implemented determination process. Illustrative algorithmic determinations may for example employ Pearson methods, Chebyshev correlation coefficients, Euclidean distance techniques, non-parametric methods, etc.

The approach of the present disclosure, involving exposure of a water sample to a test cell system to evaluate the profile of the stress responses by using a transcription factor assay, represents a major advance and numerous advantages over prior art analytic techniques in which previously identified, i.e., "listed," hazardous substances in water samples were evaluated by analytical assays to determine whether concentration of specific analyzed substances exceeded permitted levels. The biosensor-based assay of the present disclosure detects toxic substances regardless of their chemical structures or biologic composition, and can distinguish different biological effects of the toxicants on the cells of the test cell system.

Water quality determinations in accordance with the present disclosure can be carried out in computer systems, networks and apparatus that are specially adapted to perform one or more of the actions constituting the water quality assessment methods variously described herein.

The disclosure thus contemplates data acquisition, data transmission, and data processing apparatus that may be arranged to conduct, or to assist the conduct of, water quality determinations. Accordingly, the water quality determination capability, or components thereof, can be implemented as a computer system or computer program product. Computer program product embodiments include a computer program mechanism embedded or otherwise incorporated in a computer readable storage medium.

Any of the methods, or constituent actions of such methods, as variously described herein, can be embodied as a computer program product. The computer program product can be a CD-ROM, a magnetic disk storage product, or any other computer readable data or program storage product.

The software in the computer program product may also be distributed electronically, via the Internet or otherwise, by transmission of a computer data signal (in which the software modules are embedded) on a carrier wave operatively transmitted from a transmission locus device to a receiving locus device.

Computer systems or networks employed to determine water quality of unknown water samples, in accordance with the present disclosure, can include databases and/or memories containing reference transcription factor signatures for various water compositions, as a library of signatures against which specific water compositions can be compared for same or similar biosensors, to assess water quality of an evaluated water composition in relation to one or more water compositions for which transcription factors reside in the database. The water compositions in the database and/or memory can be of any suitable type for the water quality determination, e.g., distilled or otherwise purified water standards, or reference samples from earlier assays to determine longitudinal improvement or deterioration of water quality in a specific water locus such as a particular river, stream, subterranean aquifer, etc.

The database and/or memory can include any other data or information useful for conducting the water quality determination, including cellular data associated with specific transcription factor signatures, protocols for conducting the water quality determination, monitoring data logs for longitudinal studies of water quality improvement and deterioration, trans-acting factor profiles, cis-regulatory element activity profiles, bibliographies of relevant publications, research field contacts, and any other information related to water quality determinations.

Computer systems or networks employed to determine water quality of water compositions, in accordance with the present disclosure, can also include data transmission devices, components and capability, e.g., for inputting or transmitting transcription factor data, reference transcription factor signatures, etc. to the system or network, such as to a data acquisition module and/or data processing module thereof, and for outputting or transmitting transcription factor data, signatures and water quality information, for reporting or further processing purposes.

Transmission forms of data and other information in such respect can be tangible or intangible, can be embodied in texts, tables, diagrams, photographs, graphs, charts, emails, images or any other visual forms, can be recorded on a tangible media such as paper, plastic transparency sheets, film, and the like, or embodied in computer readable forms (e.g., electronic, electromagnetic, optical or other signals). Information in computer-readable form can be stored in a computer usable storage medium (e.g., CDs, optical disks, magnetic tapes, digital video discs and the like) or in computer(s) in temporary or permanent computer storage, and may reside in "raw" data (i.e., collected but unanalyzed), partially analyzed, or completed analyzed forms.

In an illustrative computer system for determining water quality in accordance with the present disclosure, the computer system includes a central processing unit, a main non-volatile storage unit such as a hard disk drive for storing software and data, controlled by a storage controller, a system memory such as high speed random-access memory (RAM) for storing system control programs, data and application programs, including programs and data loaded from the non-volatile storage unit, a system memory that may also include read-only memory (ROM), a user-interface including input devices such as a keyboard or voice input interface, a display or other output device, a network interface card for connecting to a wired or wireless communication network such as a LAN, WAN, WLAN, or Internet network, internal bus members for interconnecting components of the system, and a power source for the system.

Operationally, the aforementioned computer can be controlled primarily by an operating system that is executed by the central processing unit (CPU) of the computer system. The operating system can be stored in system memory, which may include a file system for controlling access to the various files and data structures of the computer system, a data structure for storing transcription factor signatures and related data, and a data analysis algorithm module for comparing transcription factor signatures and generating an appertaining water quality determination.

The computer system thus can comprise various software program modules and data structures, in which the data structures can comprise any form of data storage system including, without limitation, a flat ASCII or binary file, an Excel spreadsheet, a relational database (SQL), or an on-line analytical processing (OLAP) database (MDX and/or variants thereof). In particular embodiments, the data structures can each be in the form of one or more databases that include hierarchical structure and/or non-hierarchical structure, as appropriate to the system configuration and operation. The data structures may be single data structures, or they may comprise plural data structures, such as databases, spreadsheets, files, archives, etc., which may be hosted on the same computer or on different computers in a network that may be selectively accessed by a computer user.

The computer system correspondingly can include modules and data structures on one or more remote computers, and can be implemented as web-based system, e.g., in which a data analysis algorithm module and/or other modules reside on a central server that is linked in network communication with a client computer, or alternatively in which such modules reside on a client computer that is linked in network communication with a central server including a database of reference transcription factor signatures that is available to the client computer for computational determination of water quality of a specific water sample in relation to reference water standards for which reference transcription factor signatures reside on the central server in a central database library or file. The central server may for example host an interactive webpage linking to or providing computational ability for the data analysis algorithm module.

In one embodiment, the computer system and associated facilities are arranged for water quality determinations in a configuration that includes a detection facility equipped with apparatus and instrumentation for carrying out detection protocols, including RNA isolation, reverse transcription, PCR amplification, fluorescent labeling, restriction enzyme digestion, sample cleanup, capillary electrophoresis, primary data analysis and data storage. The detection facility may be operationally linked with a tissue culture facility that is compliant with biosafety requirements and is adapted to perform cell-based steps of the water quality determination, including cell storage, propagation, cell plating for screening experiments, transfection and exposure to compositions. The detection and tissue culture facilities may in turn be operationally linked to a sample handling and storage facility that performs intake, aliquotting, reformatting and storage of samples received for water quality determinations. Samples processed up a sample handling and storage facility may include stabilized cell lysates, RNA preparations, and chemical compositions. The respective detection, tissue culture and sample handling and storage facilities may be situated in an integrated manner at one geographic location, or alternatively such facilities or selected ones or components thereof may be sited remotely from other(s), as necessary or desirable in a given implementation of the computer system and associated facilities.

The present disclosure also contemplates the provision of various kits as useful for carrying out water quality determinations for unknown water samples.

In one embodiment, the kit comprises transcription factor signatures for reference library water compositions in a graphical format, to facilitate threshold visual determinations of a transcription factor signature to reference of an unknown water sample in relation library signatures, e.g., as a toxicological or epidemiological tool to quickly rule in or rule out environmental and etiological contaminants in water samples, on the basis of perceived visual similarity or dissimilarity of graphical format transcription factor signatures in relation to reference library signatures.

In another embodiment, the kit comprises biosensors, e.g., specific cell line cells that have been transfected with reporter transcription units, and contacting containers in which the cells may be contacted with unknown water samples, together with instructional documents containing protocols for conducting the contacting operation, and the further processing of the contacted cell samples for analysis of transcription factor signatures. Kits in other embodiments may comprise, or further comprise, lyzing media, transfection vectors, restriction enzymes, reverse transcription reagents, PCR primers, fluorescent dyes, discs or flash drives containing capillary electrophoresis data processing software, transcription factor signature-generation software, and/or software for conducting other of the component operations in the water quality determination.

In still other embodiments, kits may be constituted with any one or more of the foregoing kit components.

The features and advantages of the systems and methods of the present disclosure are more fully shown with respect to the following non-limiting drawings figures and appertaining description.

FIG. 1 is a schematic representation of an illustrative water quality assay system 10, according to one embodiment of the present disclosure. The system 10 includes a transcription factor signature data acquisition module 12 operationally linked in information transmission relationship, by information transmission link 16, to transcription factor signature data analyzer module 14 adapted to output information 22 related to the water quality assay determination for the test water sample composition 18 introduced to the transcription factor signature data acquisition module 12. Such output information 22 from transcription factor signature data analyzer module 14 may for example comprise water quality report for the test composition 18, e.g., in relation to reference composition 20 introduced to the transcription factor signature data acquisition data module 12. Alternatively, the output information 22 from the transcription factor signature data analyzer module 14 may comprise a data signal that is further processed to generate a water quality determination, such as by input to a network for communication to a central server adapted to generate such water quality determination, and to communicate such determination back to the transcription factor signature data analyzer module 14 and/or to other devices coupled by wired or wireless connections to the network.

Figure 2:
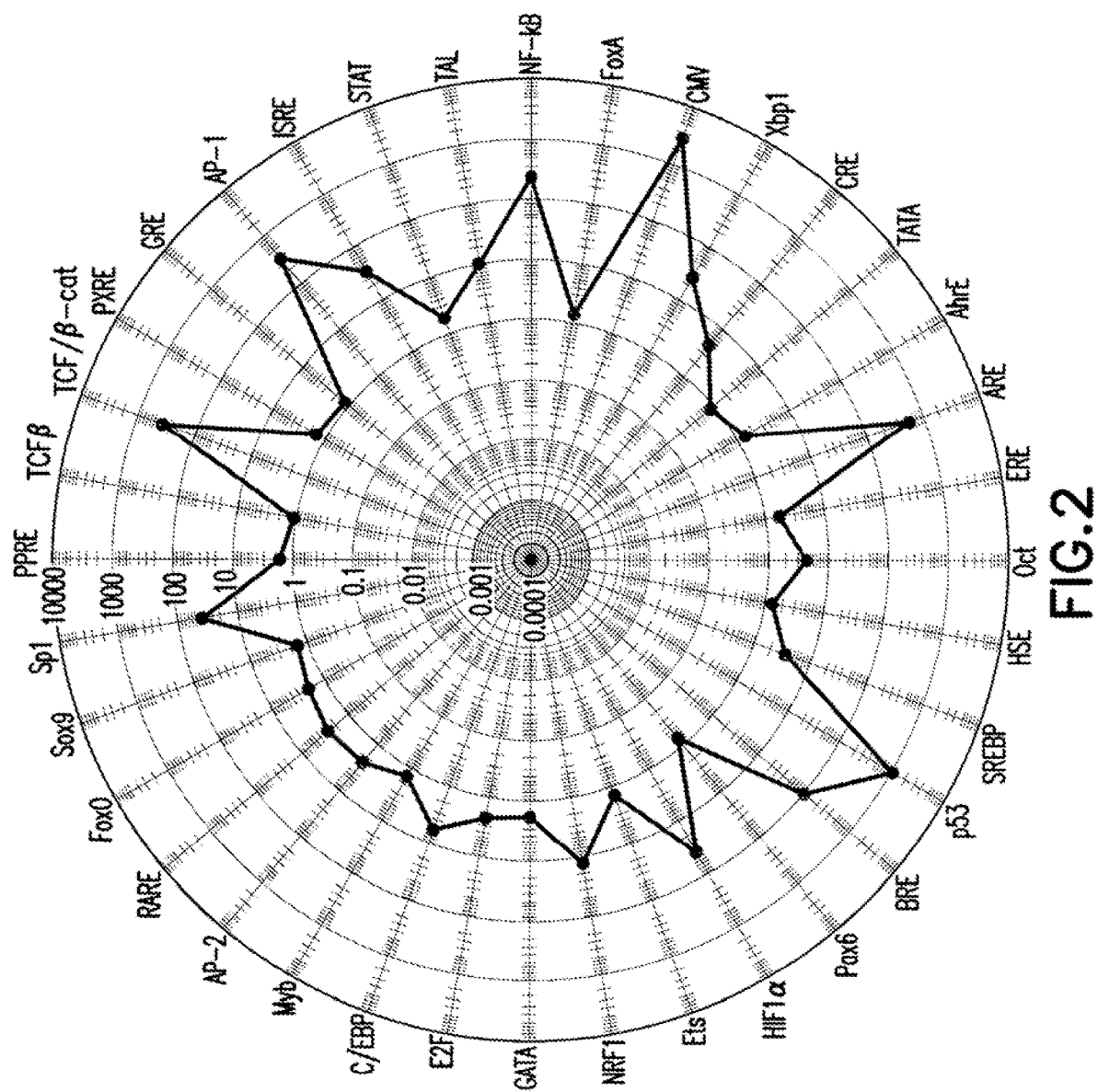
FIG. 2 is a polar coordinate graphical representation of capillary electrophoresis data showing relative fluorescent values of reporter peaks indicative of transcription factor activity, as a function of transcription factor species, in which the transcription factor activity is the activity generated by interaction of a water composition of interest with a host cell containing reporter transcription factor units for each of the transcription factor species shown on the graph.

FIG. 2 is a polar coordinate graphical representation of capillary electrophoresis data showing relative fluorescent values of reporter peaks indicative of transcription factor activity, as a function of transcription factor species, in which the transcription factor activity is the activity generated by interaction of a water sample of interest with a host cell containing reporter transcription factor units for each of the transcription factor species shown on the graph.

The transcription factor activity graph of FIG. 2 shows the fluorescence peaks of the activated transcription factors as radially outwardly projecting from a baseline circle representing a non-activated state of corresponding transcription factors whose data points appear at the baseline circle, and with the radial extent of the fluorescence peaks being in arbitrary fluorescence units. In this graph, 36 transcription factors have been assayed, and their alphabetic designations appear around the outer periphery of the polar graph.

It is evident from visual inspection of the graph that the transcription factors Sp1, TCF/βcat, AP-1, ISRE, TAL, NF-κB, CMV, Xbp1, CRE, ARE, Oct, SREBP, p53, BRE, HIF-1α, NRF1, and C/EBP show increased activity in relation to the other transcription factors, and that the polar graph provides a "fingerprint" of the interaction of the transcription factor units-containing host cell and the water sample of interest.

Accordingly, by comparison of the transcription factor signature on each of respective polar graphs, with respect to peak coordinates specifying a radial distance from the base circle, comparisons of water quality of difference samples used to generate the corresponding graphs can be quantitatively ascertained from the relational congruence of the respective transcription factor signature graphs for such water samples.

Figure 3:
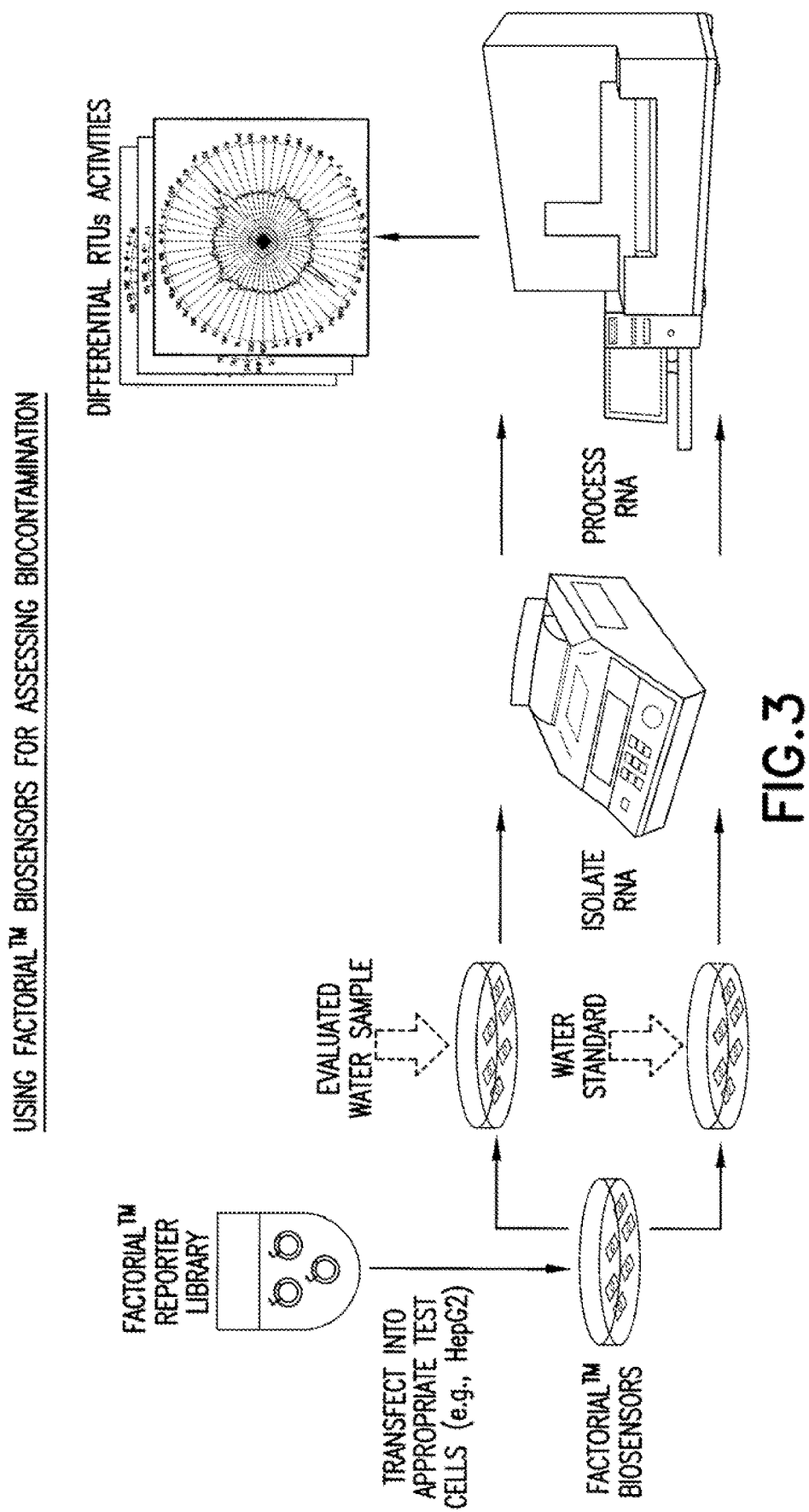
FIG. 3 is a schematic depiction of the process of generating a transcription factor signature for a host cell biosensor in exposure to an evaluated water sample and water standard.

FIG. 3 is a schematic depiction of the process of generating a transcription factor signature for a host cell biosensor in exposure to an evaluated water sample. As shown, a reporter library ("FACTORIAL™ reporter Library") including plasmid constructs incorporating reporter transcription factor units is transfected into appropriate test cells, e.g., HepG2 cells, to form a biosensor cell population ("FACTORIAL™ biosensors"). The biosensor cell population is then exposed to the "evaluated water sample," i.e., the water composition for which the transcription factor signature is to be generated, as well as exposure of the biosensor cell population to the "water standard," as the reference water specimen for comparison purposes. After exposure to the evaluated substance, reporter RNA produced in the cell by action of the reporter transcription units in the transfecting plasmids is isolated from the exposed biosensor cells. As previously described, the amounts of the respective RNAs are commensurate with the activities of the corresponding transcription factors present in the transfected cell(s) in response to the exposure to the evaluated water sample, and to the water standard.

The isolated RNAs tagged with variably positioned cleavage site tags are processed by reverse transcription to form reporter cDNAs that are amplified by PCR using a primer pairs that are common for all reporters, following which the PCR products are labeled with fluorescent dye and contacted with restriction enzyme to produce a distribution of fluorescent labeled DNA fragments of different lengths. These different length fragments are resolved by capillary electrophoresis and detected as separate fluorescent peaks.

The transcription factor signature then is generated in polar coordinate graphs of the fluorescent peaks that in the aggregate reflect the profile of changes in activities of the reporter transcription units ("Differential RTUs activities"). In this manner, the biosensors are employed for assessing the imprint of a water sample on activities of multiple transcription factors in test cells, i.e., the transcription factor signature for that water sample (evaluated water sample or water standard).

FIG. 4 shows a tabulation listing of identified reporter transcription units, the corresponding induction transcription factors, and prototypic, and associated biological pathways. cis-FACTORIAL™ assay thus comprises profiling of more than 50 transcription factor families in a single well of test cells using the reporter transcription factors as described in Romanov, S., et al., Nature Methods (2008).

Figure 5:
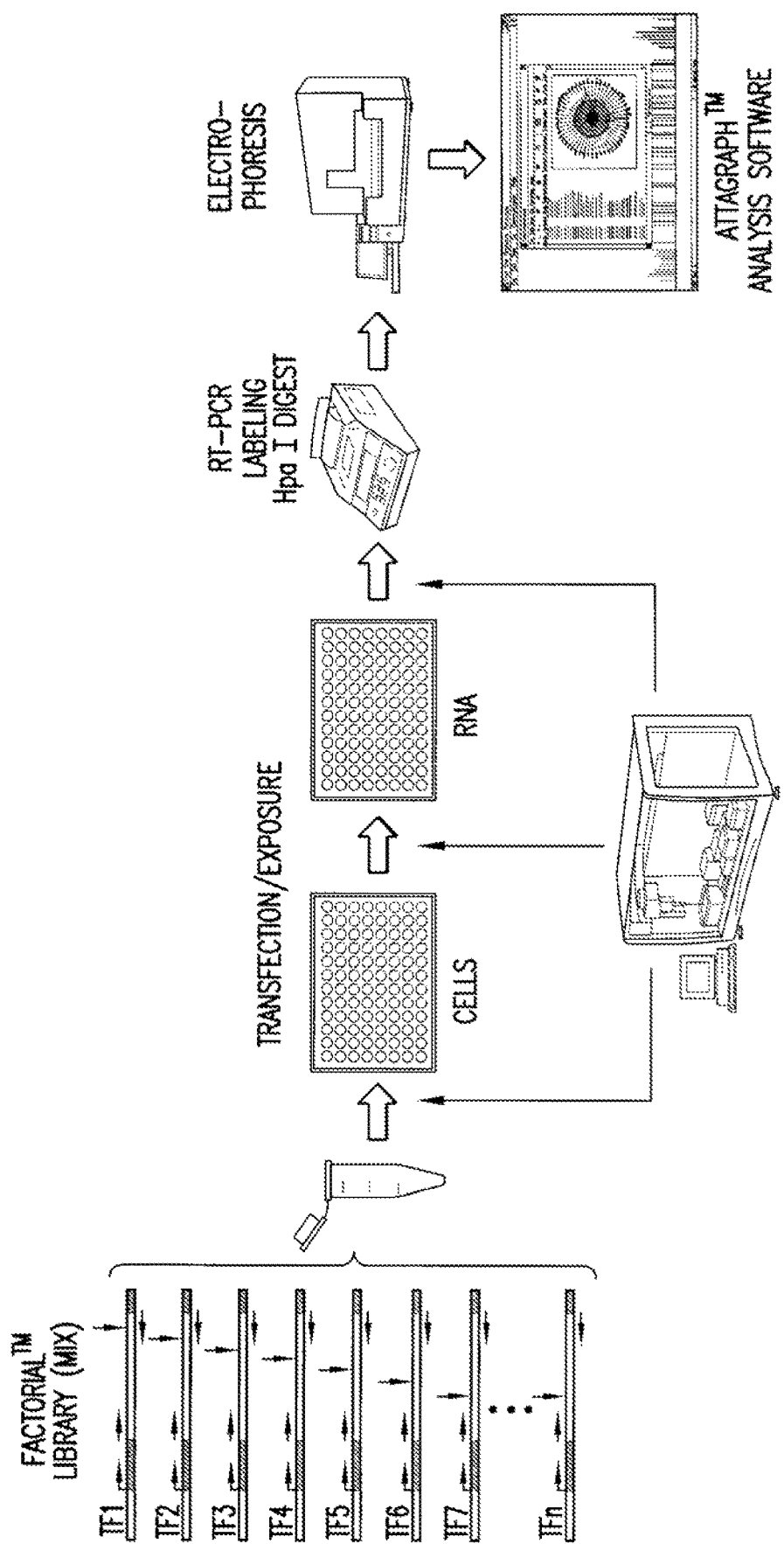
FIG. 5 is a schematic representation of a transcription factor signature generation process, in which a library of reporter transcription units (FACTORIAL™ library (mix)) comprising reporter transcription factor units TF1, TF2, ... , TFn are transfected into appropriate test cells, e.g., HepG2 cells, to form a biosensor cell population.

FIG. 5 is a schematic representation of a transcription factor signature generation process, in which a library of reporter transcription units (FACTORIAL™ library (mix)) comprising reporter transcription factor units TF1, TF2, . . . , TFn are transfected into appropriate test cells, e.g., HepG2 cells, to form a biosensor cell population. The biosensor cell population then is exposed to a water sample for which the transcription factor signature is to be generated. After exposure, reporter RNA produced in the cells by action of the reporter transcription units is isolated from the biosensor cell, following which the isolated RNAs are processed by reverse transcription, polymerase chain reaction (RT-PCR) and the PCR products are labeled with fluorescent dye and contacted with the restriction enzyme (HpaI) to produce distribution of fluorescently labeled DNA fragments of different lengths that are then processed by electrophoresis. The resolved different length fragments are detected in the electrophoresis operation as separate fluorescent peaks in a polar coordinate radar graph, with FIG. 5 showing an outputted graph generated by action of the analysis software (ATTAGRAPH™ Analysis Software). This polar coordinate graph of the fluorescent peaks is the transcription factor signature for the specific water sample employed in the exposure of the test cells, and represents the profile of changes of activities of the reporter transcription units as a result of the exposure to the specific water sample.

FIG. 6 is a simplified schematic diagram of the process described in connection with FIG. 5. As shown in FIG. 6, the library of reporter transcription units (RTUs) includes differently positioned restriction enzyme cleavage sites, together with an appertaining promoter. Such RTUs constructs then generate corresponding reporter RNA in the test cells upon exposure to the water sample of interest, and the reporter RNA then is isolated and utilized to form reporter cDNAs that are amplified, labeled and digested to form the labeled fragments submitted to electrophoresis, generating a corresponding electrophoresis spectrum and an output radar graph of the transcription factor signature (OUTPUT).

By such process, a suitable number of stress-response and toxicity pathways of the test cells can be evaluated. For example, an appropriate number of reporter transcription units can be employed for evaluation of 10, 20, 30, 40, 50 or more such pathways. For example, the pathways may include the pathways illustratively identified below:

| EVALUATION OF 40+ stress-response and toxicity pathways: | |
|---|---|
| NF-kappaB, AP-1 | (inflammatory responses) |
| HIF-1alpha | (hypoxia stress response) |
| ARE/NRF-2 | (oxidative stress) |
| P53 | (genotoxic stress) |
| HSP | (heat-shock) |
| AhR | (dioxin response) |

Figure 7:
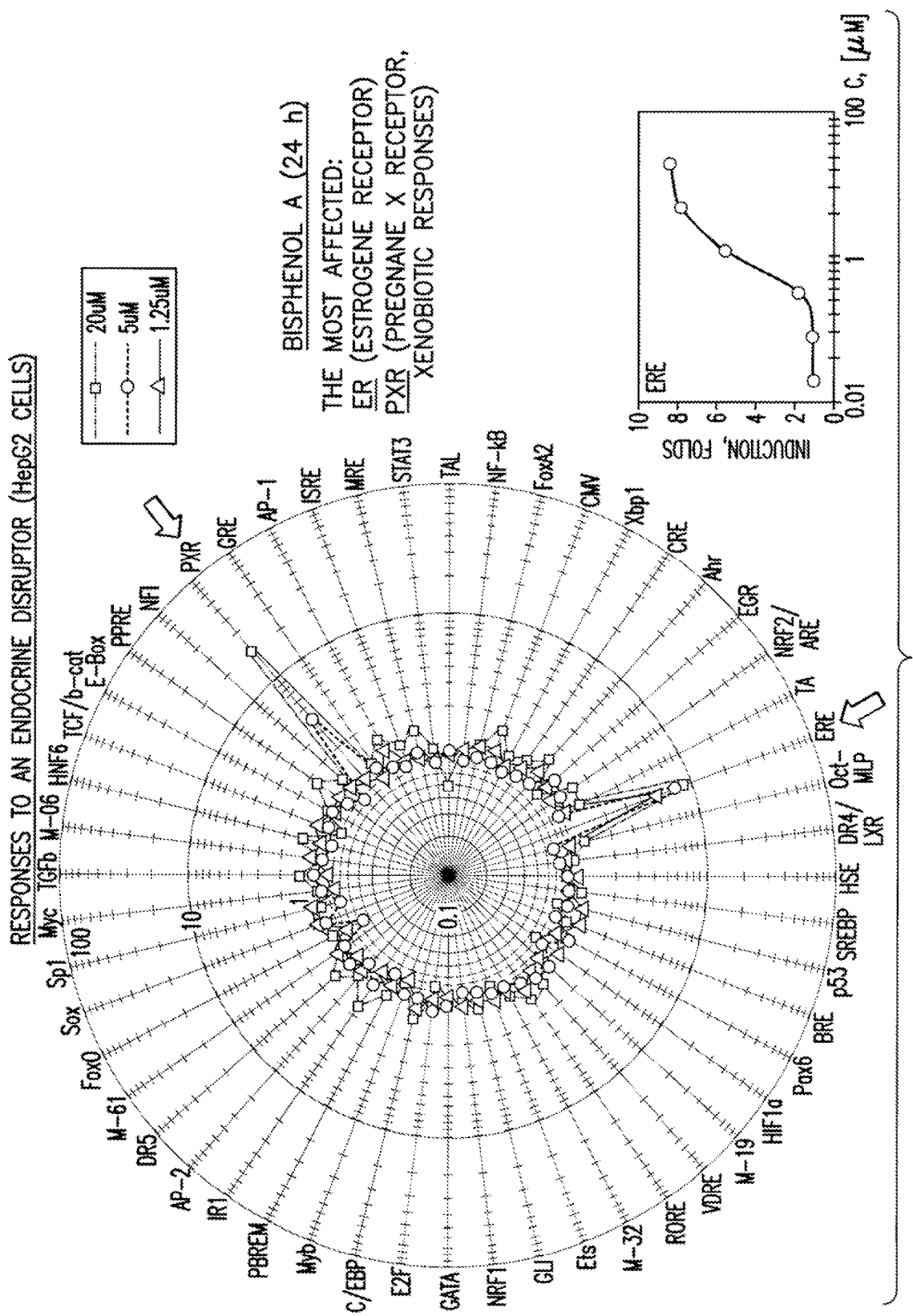
FIG. 7 is a polar coordinate radar graph for response of test cells to an endocrine disruptor, using a HepG2 cells in the test cell system, in exposure to bisphenol A, which is known to affect estrogene receptors (ER) and pregnane X receptors (PXR) and xenobiotic responses.

FIG. 7 is a polar coordinate radar graph for response of test cells to an endocrine disruptor, using a GPG2 cells in the test cell system, for bisphenol A, which is known to effect estrogene receptors (ER) and pregnane X receptors (PXR) and xenobiotic responses.

The radar graph of FIG. 7 is a composite graph with individual data spectra obtained at concentrations of 20 µM, 5 µM and 1.25 µM, 24 hours after test cell system exposure to bisphenol A. Also set out in FIG. 7 is an induction folds plot for this assay.

Figure 8:
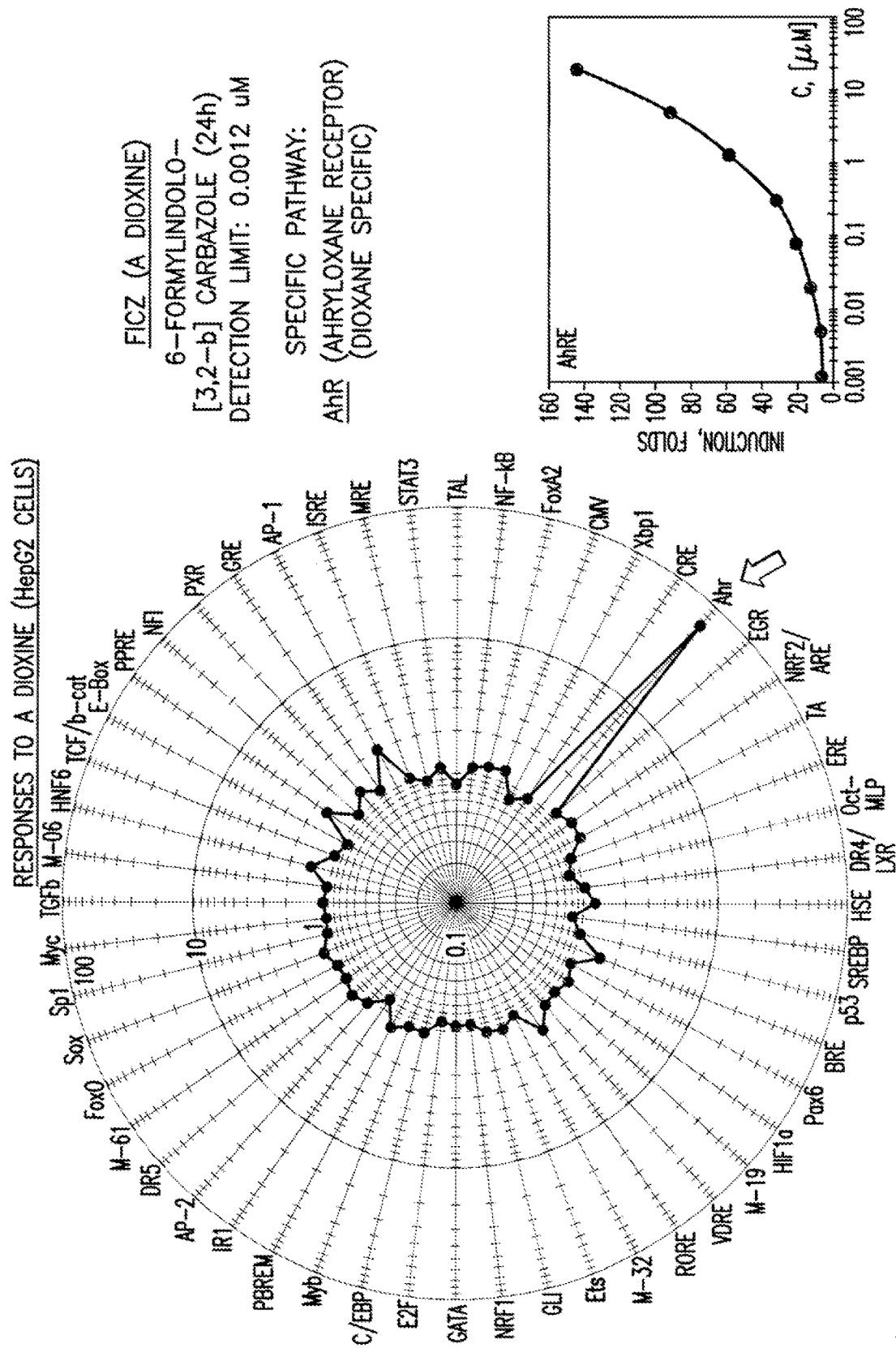
FIG. 8 shows a radar graph for test cell system transcription factor signature, for cellular response to a dioxine in HepG2 cells.

FIG. 8 shows a radar graph for test cell system transcription factor signature, for cellular response to a dioxine in HepG2 cells. The dioxine in this assay was 6-formylindolo-[3,2-b]carbazole, in which the transcription factor signature was determined after 24 hours exposure to the dioxine.

FIG. 8 also shows the induction folds plot for this assay. The specific pathway shown by fluorescence peak manifestation is the Ahryloxane receptor (AhR) as being dioxane specific in character.

Figure 9:
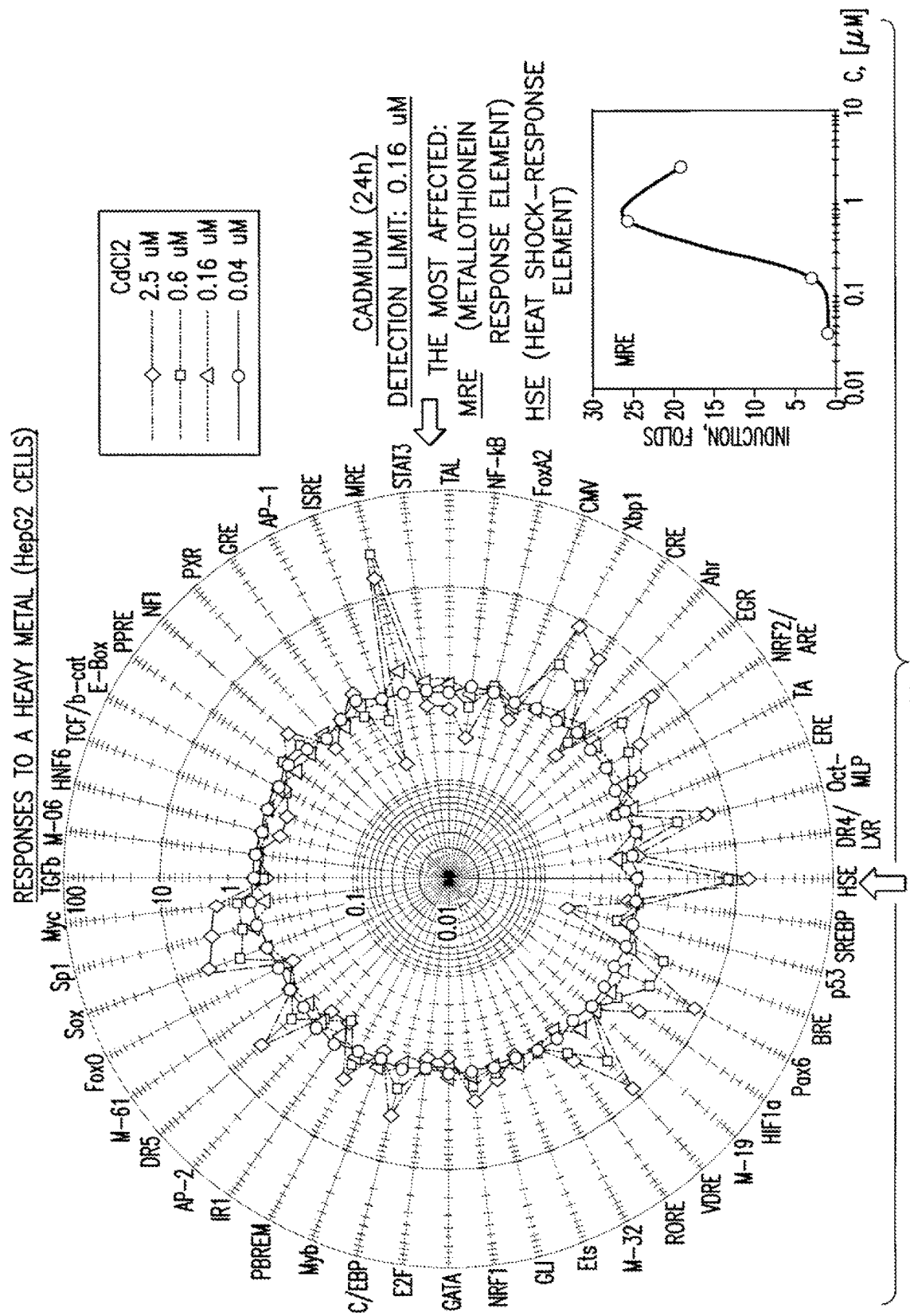
FIG. 9 shows a radar graph for transcription factor signatures in response to a heavy metal, cadmium, as determined for cellular response 24 hours after exposure.

FIG. 9 shows a radar graph for transcription factor signatures in response to a heavy metal, cadmium, as determined for cellular response 24 hours after exposure. The cadmium exposure involved contacting the cells and the test cell system with cadmium dichloride with successive assays being performed to generate respective transcription factor profiles at concentrations of 2.5 µM, 0.6 µM, 0.16 µM and 0.04 µM. The assay showed that the cellular response was most pronounced for the metallothionein response element (MRE) and the heat shock-response element (HSE). The induction folds plot is included in FIG. 9.

Figure 10:
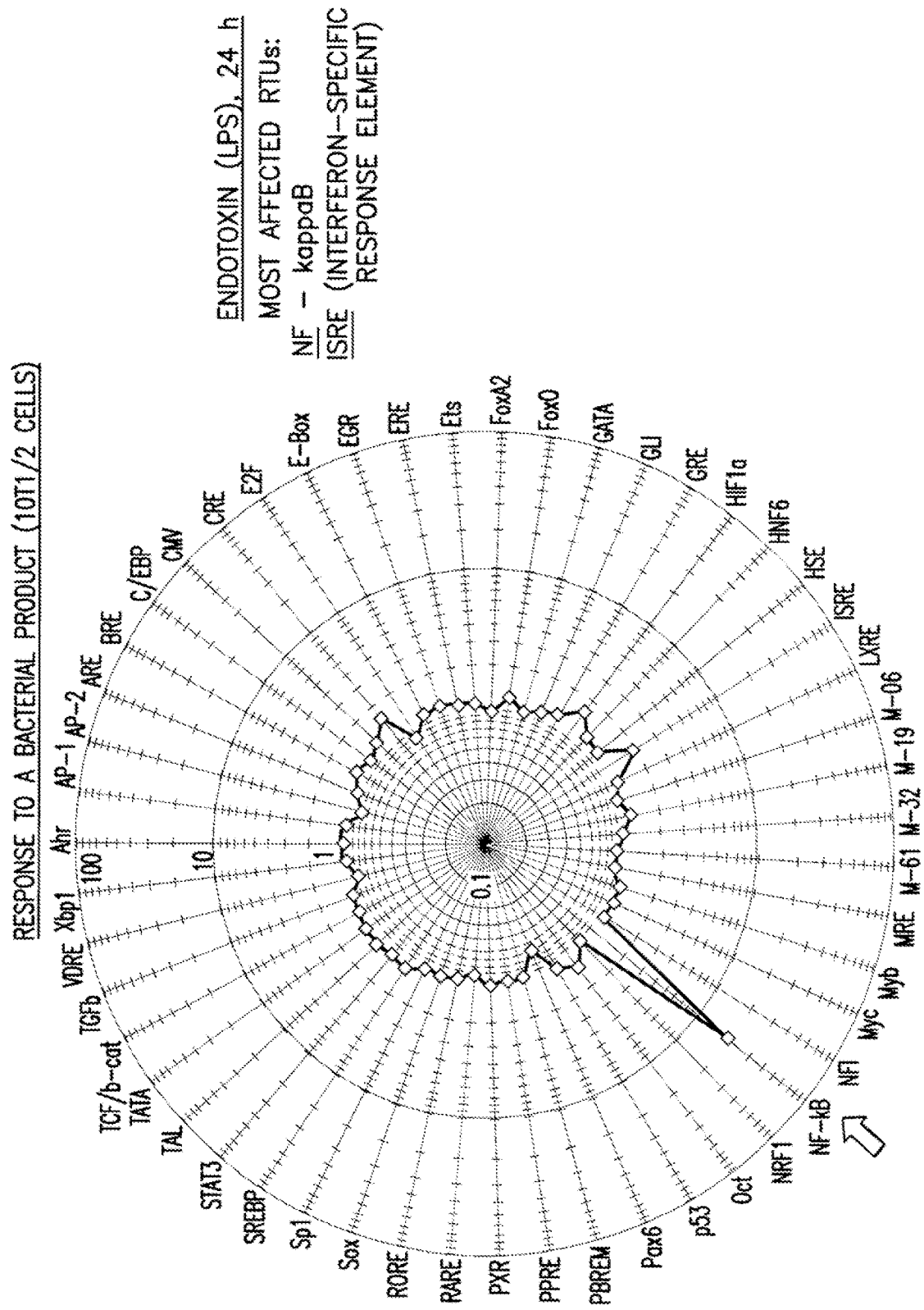
FIG. 10 is a polar coordinate radar graph showing transcription factor signature for response of the test cell system cells to endotoxin (lipopolysaccharide, LPS), 24 hours after exposure.

FIG. 10 is a polar coordinate radar graph showing transcription factor signature for response of the test cell system cells to endotoxin (lipopolysaccharide, LPS), 24 hours after exposure. This assay therefore shows the response spectrum of cells following exposure to a bacterial toxin, showing the most affected reporter transcription units to be NF-kappaB and Interferon-specific response element (ISRE).

Figure 11:
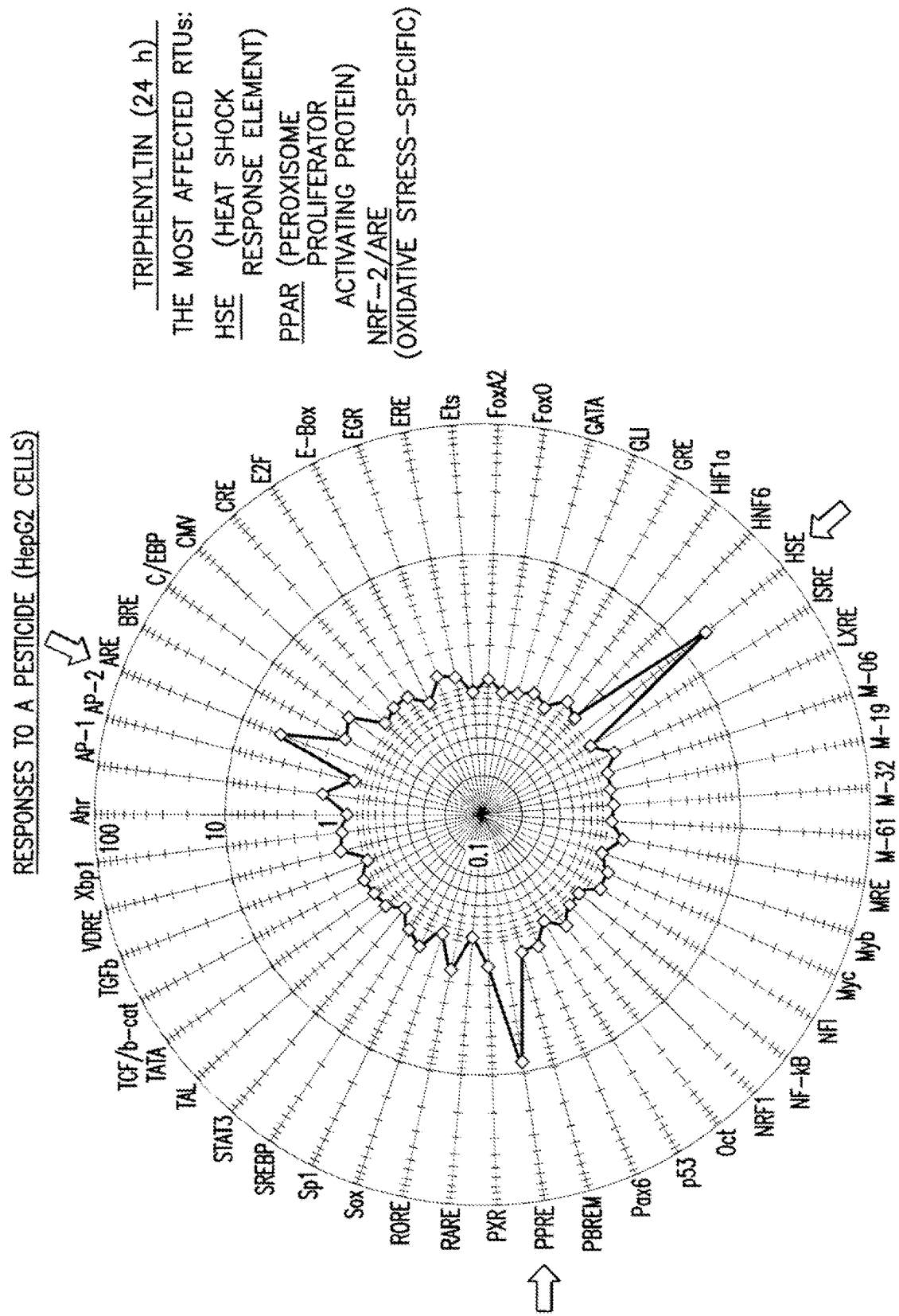
FIG. 11 is a polar coordinate radar graph for response of cells in the test cell system to a pesticide, triphenyltin, after 24 hours from initial exposure.

FIG. 11 is a polar coordinate radar graph for response of cells in the test cell system to a pesticide triphenyltin, after 24 hours from initial exposure, showing the most affected reporter transcription units to be the cellular heat shock response element (HSE), the peroxisome proliferator activating protein (PPAR) and the oxidative stress-specific RTU, NRF-2/ARE.

The foregoing transcription factor signatures reflect quantifiable indicia of cellular exposure and response. Corresponding water samples containing such contaminants are therefore susceptible to assay in which the contamination of the water specimen is readily detectable and can be assessed in a manner permitting reproducible characterization of the water quality testing operation.

Biocontamination of water can thereby be quantitatively assessed in a suitable manner. In one embodiment, the quantitative assessment of biocontamination is carried out as an integral function of individual stress-responses, utilizing each of the stress-responses in the assay for calculation of a biocontamination rating, which algorithmically may be stated as:

$$\text{Biocontamination} = \Sigma(\log K_i)^2 = (\log K_1)^2 + (\log K_2)^2 + (\log K_3)^2 + \ldots (\log K_N)^2$$

wherein K is the value of the stress-response for a specific stress response pathway, i.

By such algorithmic characterization, the biocontamination of specific ones of multiple water samples can be characterized against water quality standards as well as against one another.

Figure 12:
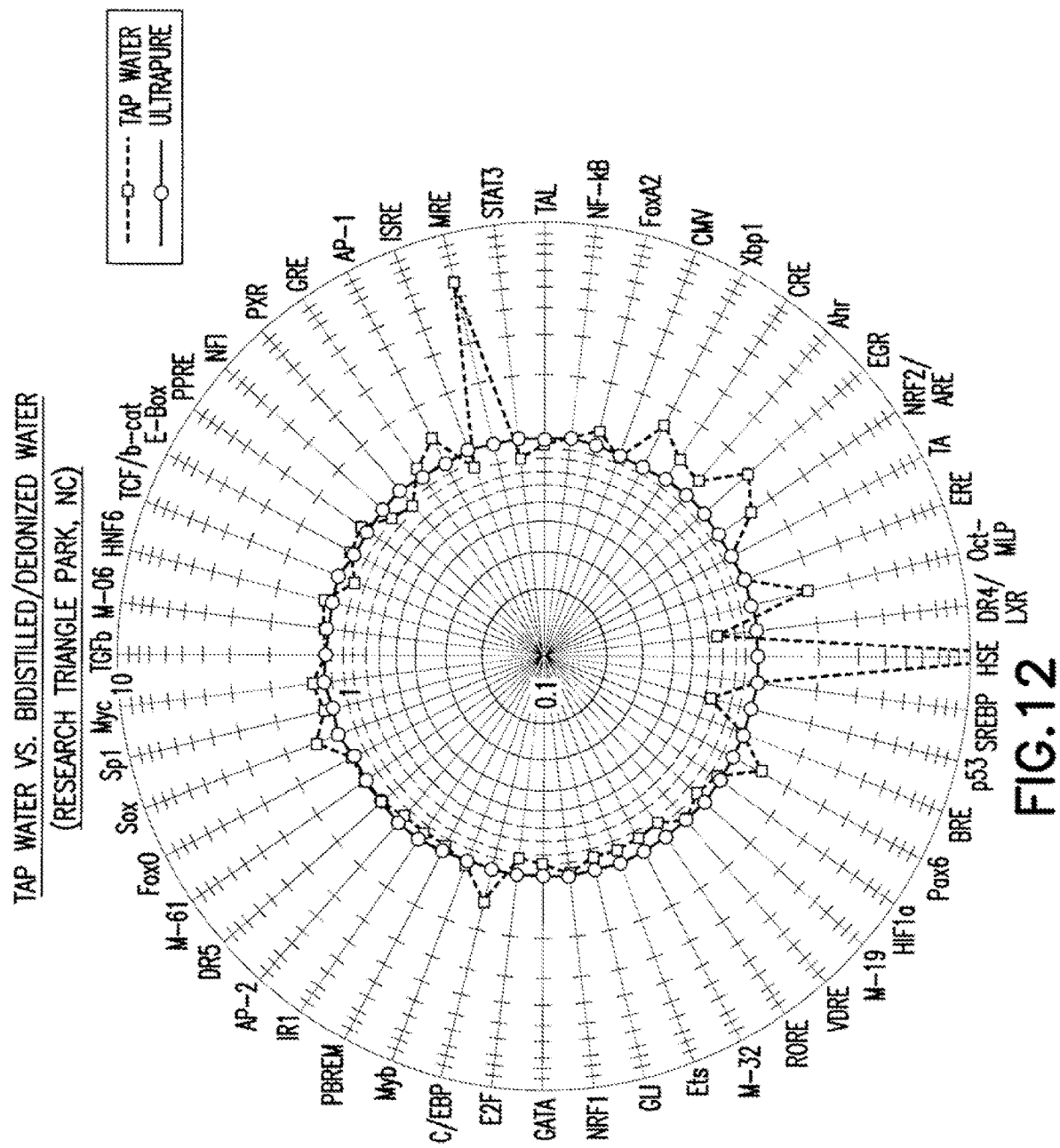
FIG. 12 shows a transcription factor signature graph for tap water and for ultra pure (bidistilled/deionized) water sampled at Research Triangle Park, N.C., and exposed to a test cell system comprising human hepatocytic HepG2 cells.

FIG. 12 shows a transcription factor signature graph for tap water and for ultra pure (bidistilled/deionized) water sampled at Research Triangle Park, N.C., and exposed to a test cell system comprising human hepatocytic HepG2 cells, showing the comparative character of tap water versus purified water at such geographic location.

Figure 13:
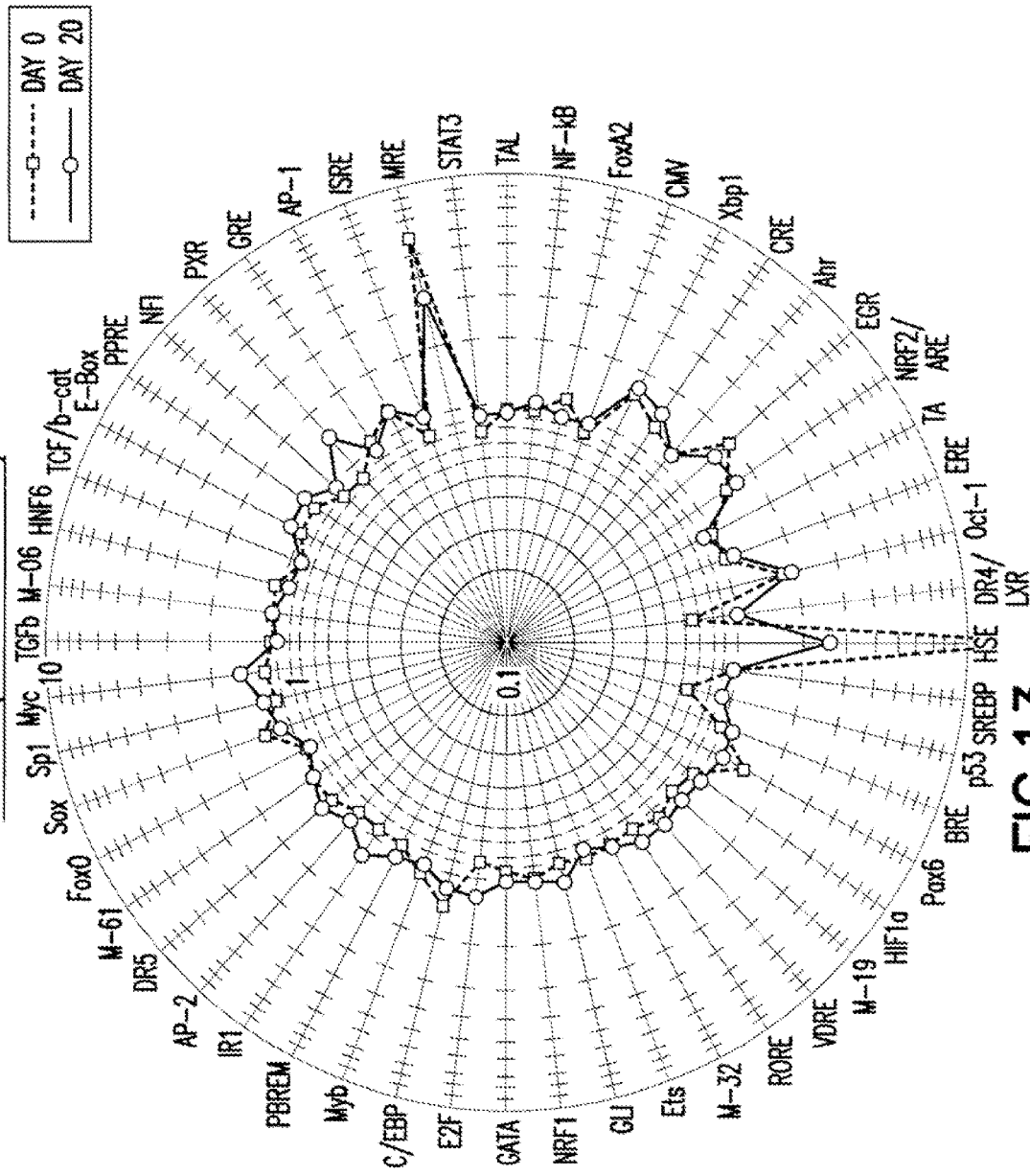
FIG. 13 is a radar graph for a repeated assessment of the tap water sample whose signature is shown in FIG. 12, after prolonged storage (20 days at 40° C.).

FIG. 13 is a radar graph for a repeated assessment of the tap water sample whose signature is shown in FIG. 12, after prolonged storage (20 days at 40° C.). Signature data is shown at day 0 and day 20.

Thus, as shown by FIGS. 12 and 13, longitudinal studies can be made of water quality utilizing the methodology of the present disclosure.

Figure 14:
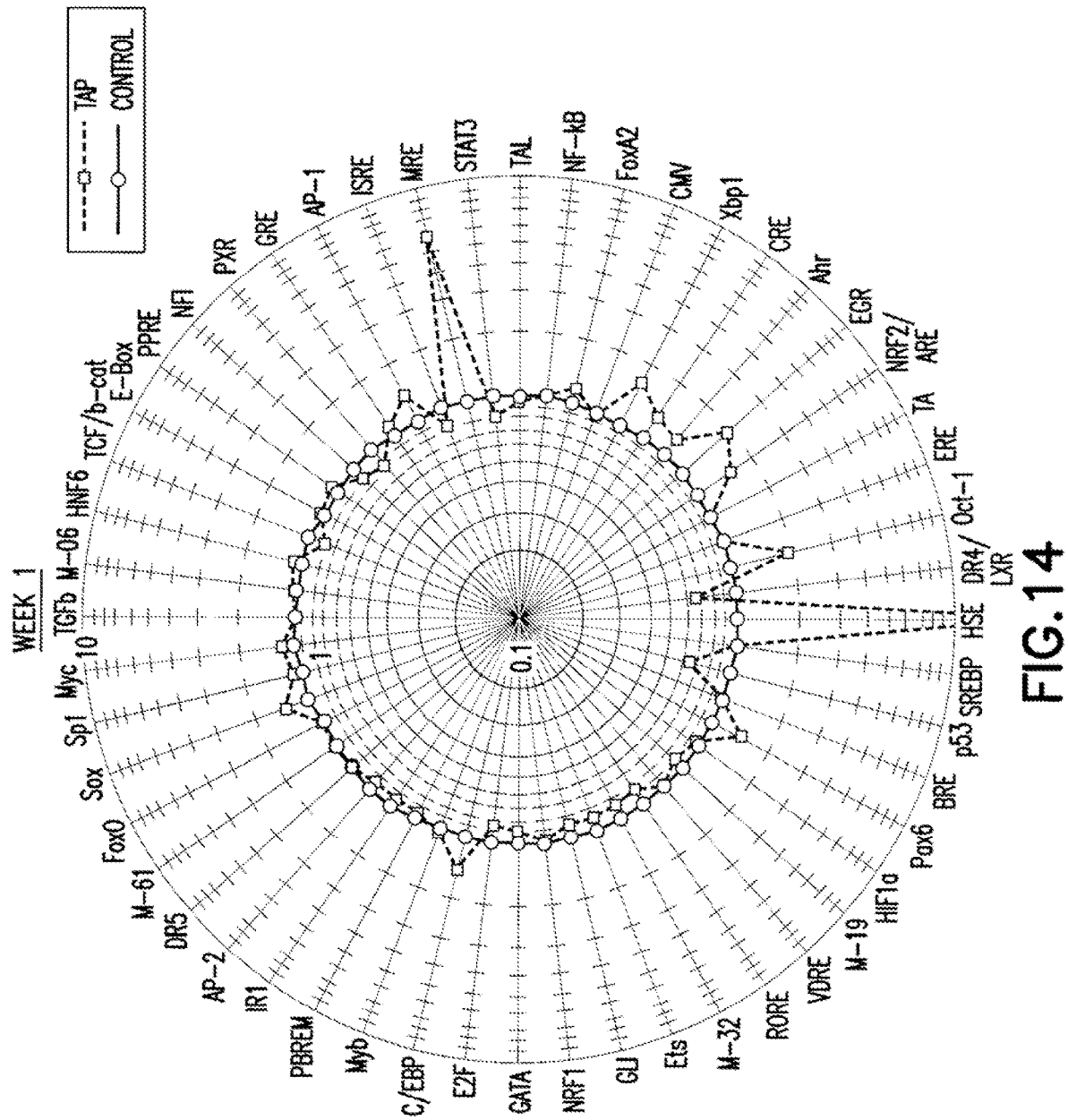
FIGS. 14, 15, 16 and 17 show tap water and purified control water signatures over a time frame of four weeks.
Figure 15:
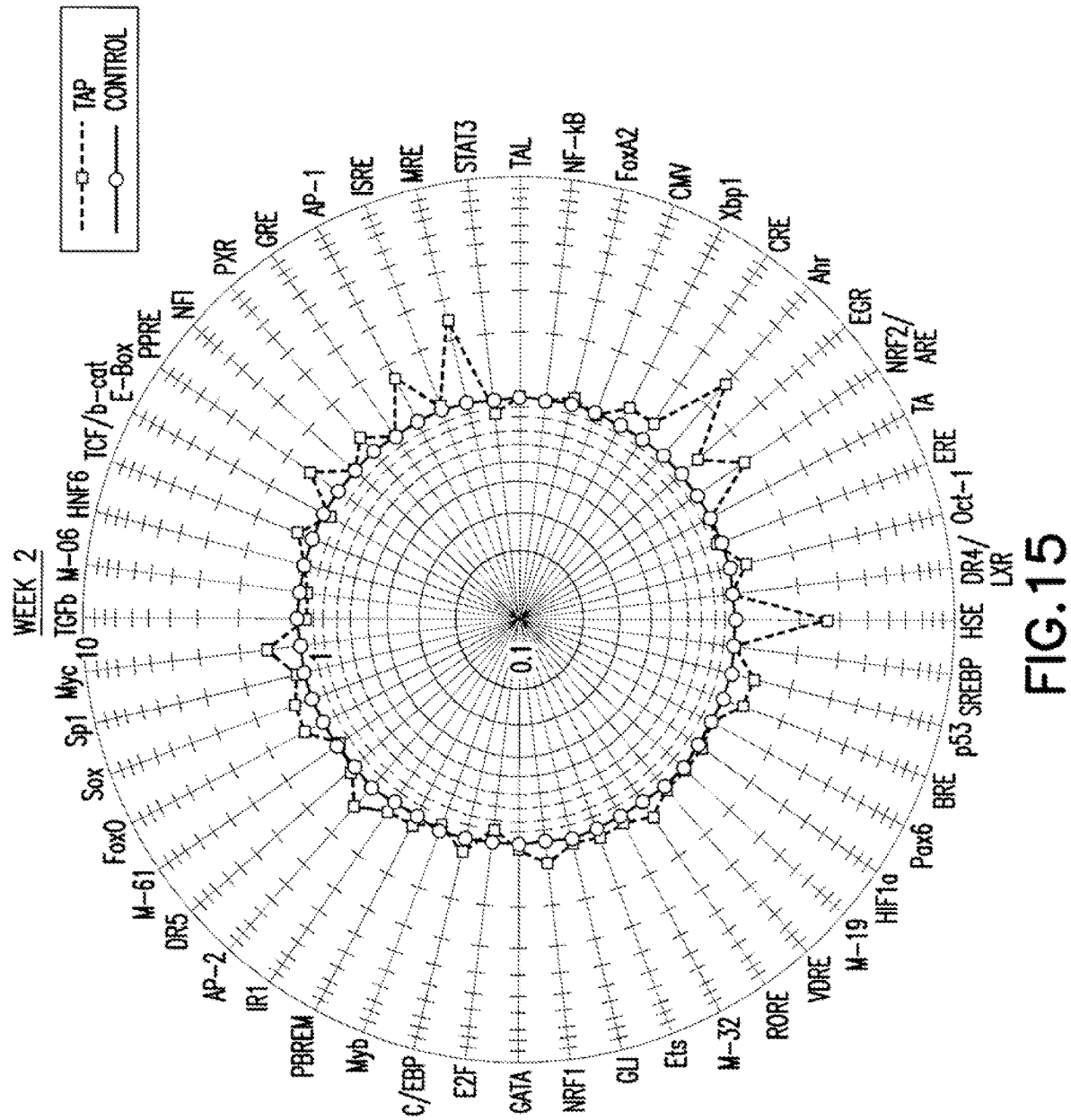
Figure 16:
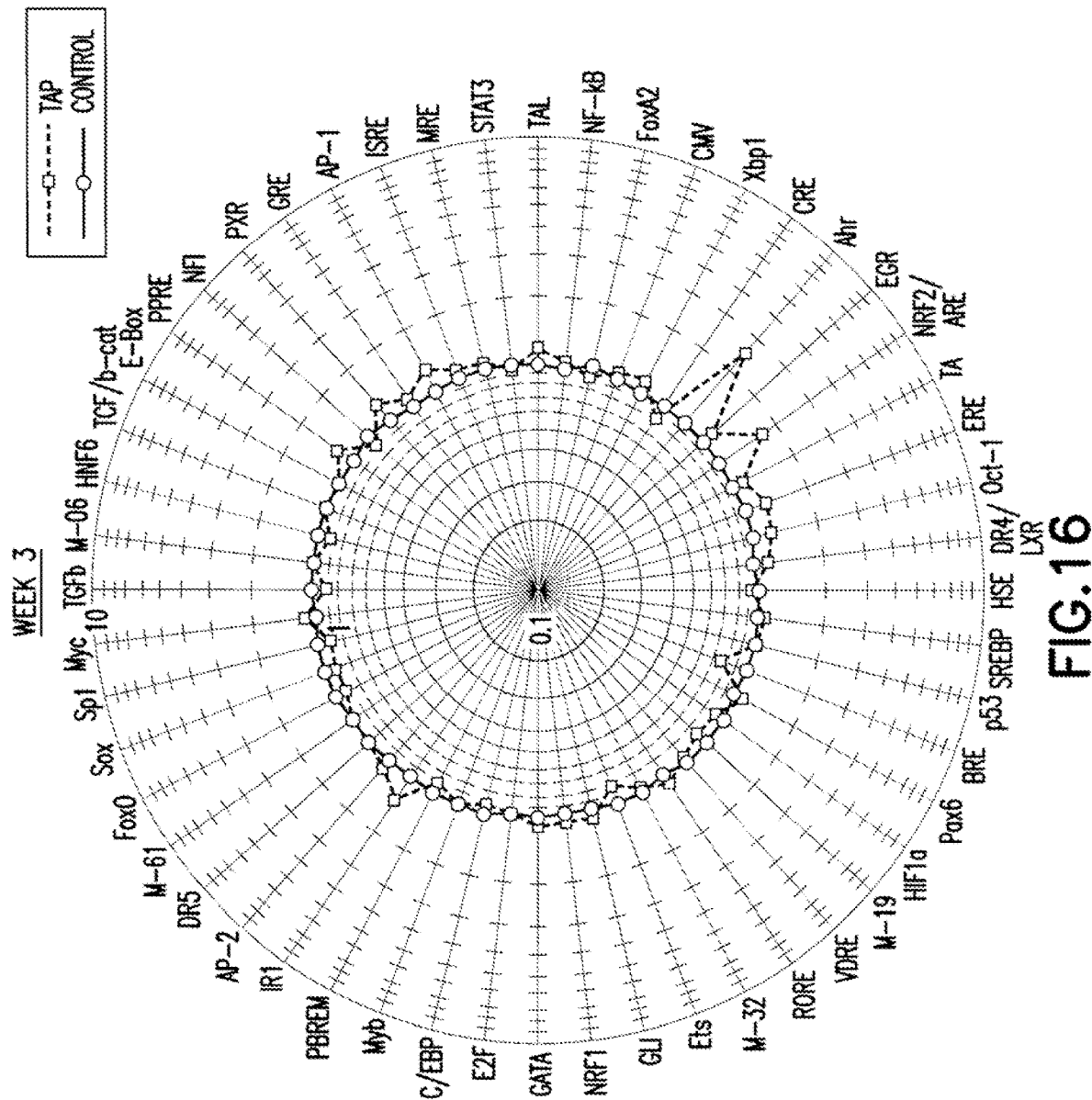
Figure 17:
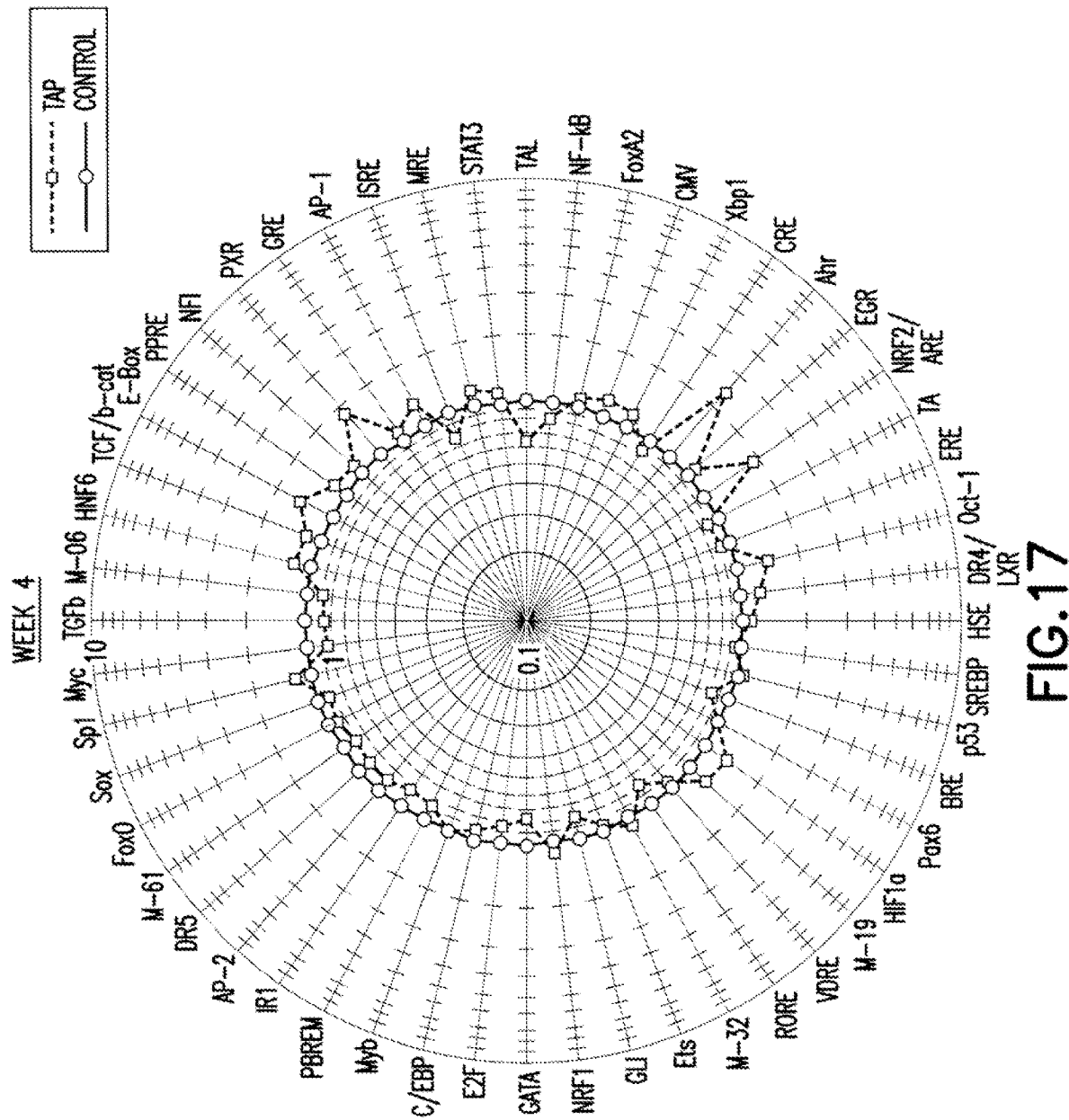

FIGS. 14, 15, 16 and 17 show tap water and purified control water signatures over a time frame of four weeks, with FIG. 14 showing signature data at week 1, FIG. 15 showing signature data at week 2, FIG. 16 showing signature data at week 3 and FIG. 17 showing signature data at week 4. In this assessment, evaluated tap water samples were collected weekly from a same faucet, and show changes in tap water contamination over the appertaining time frame.

Figure 18:
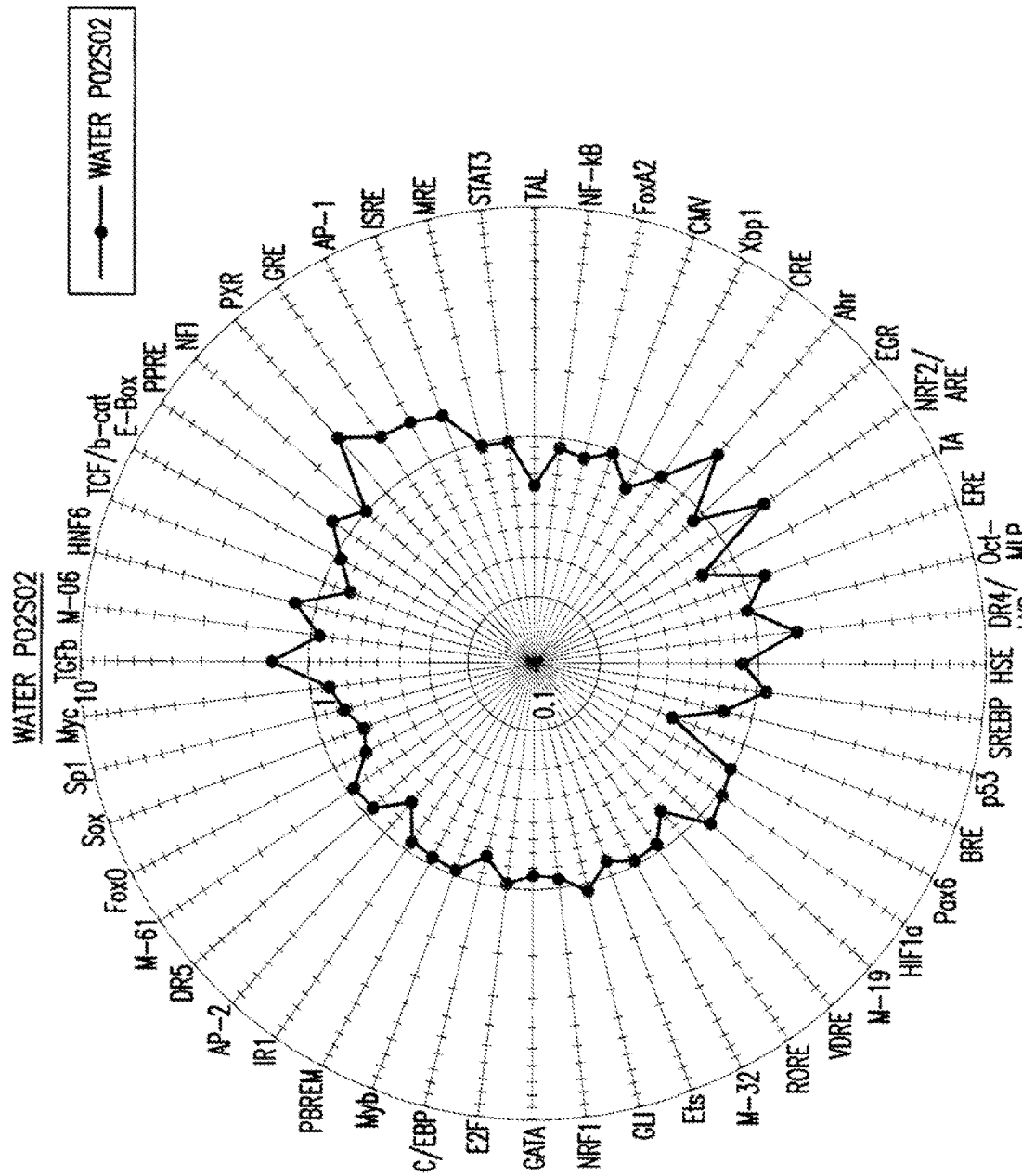
FIGS. 18-22 show tap water quality at selected geographic locations in the United States, in respective transcription factor signatures in the illustrated radar graphs.
Figure 19:
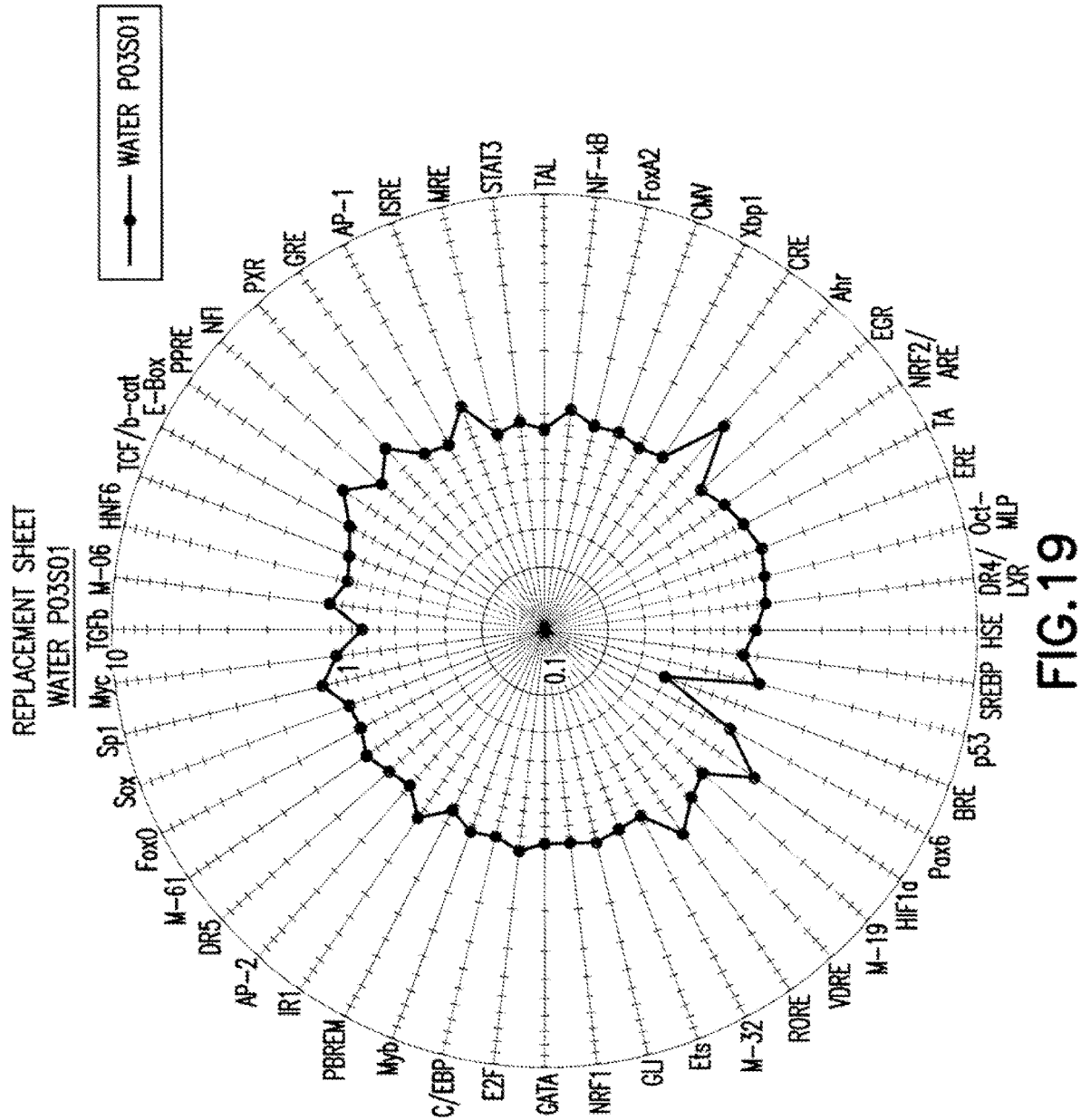
Figure 20:
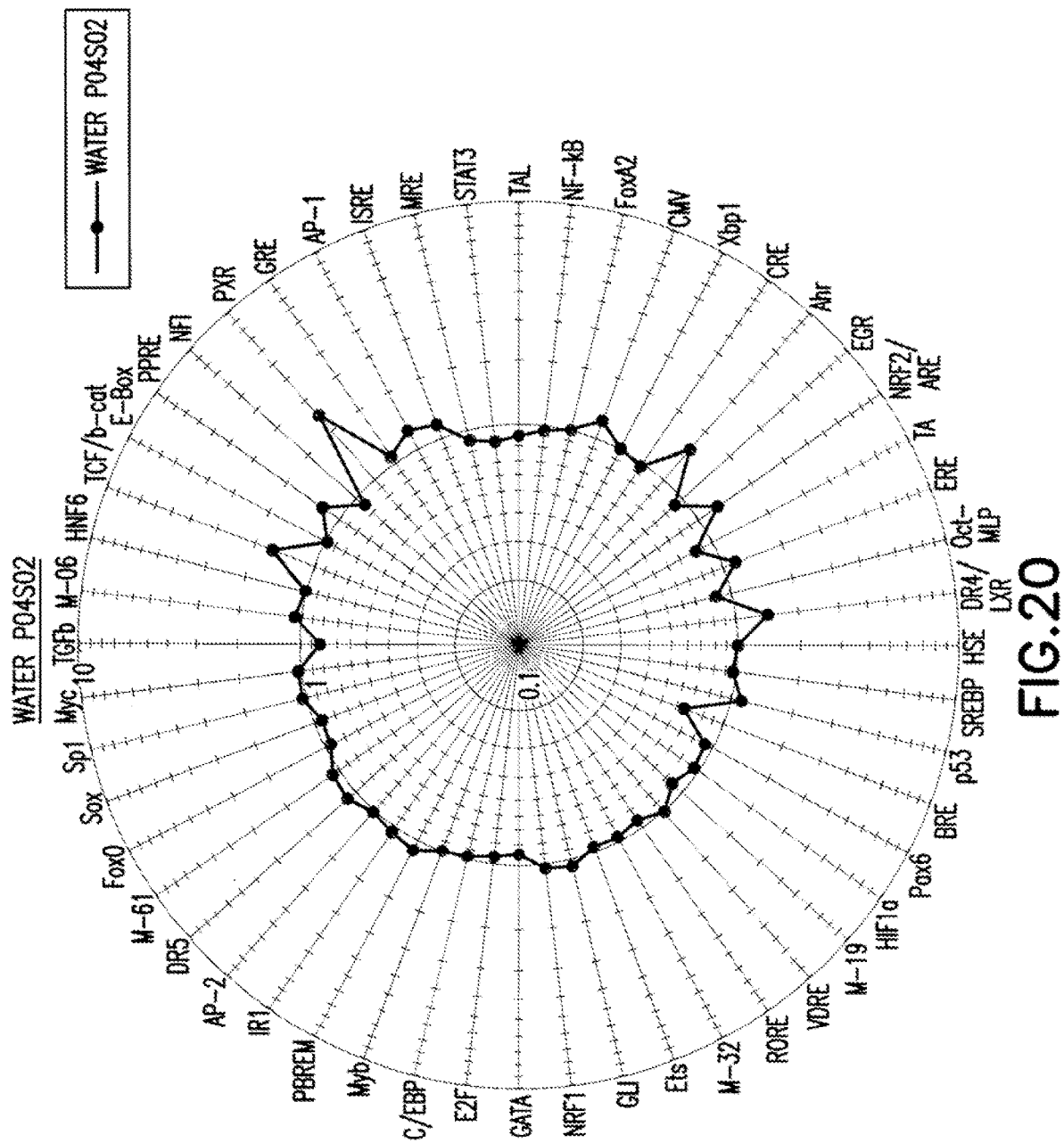
Figure 21:
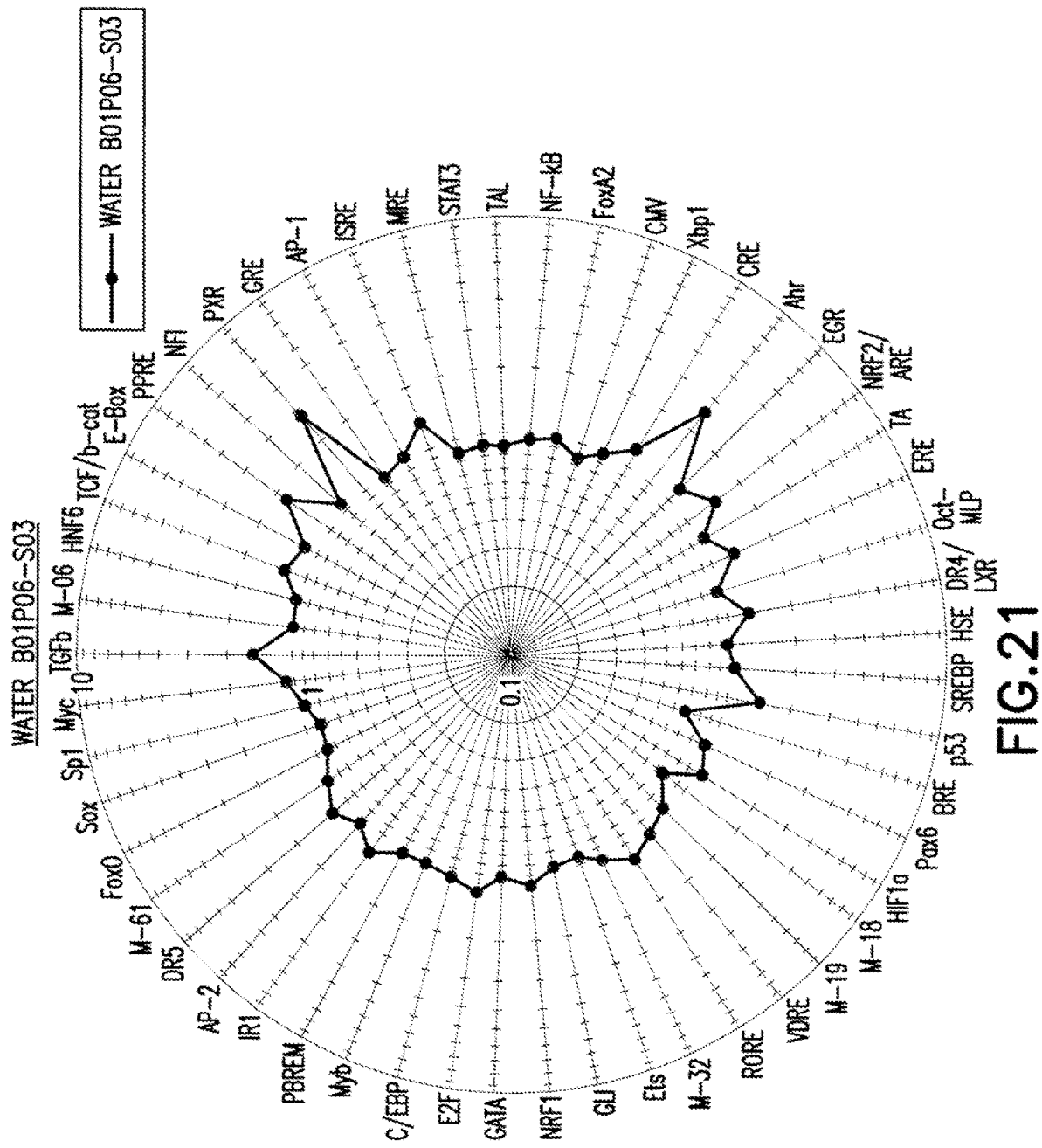
Figure 22:
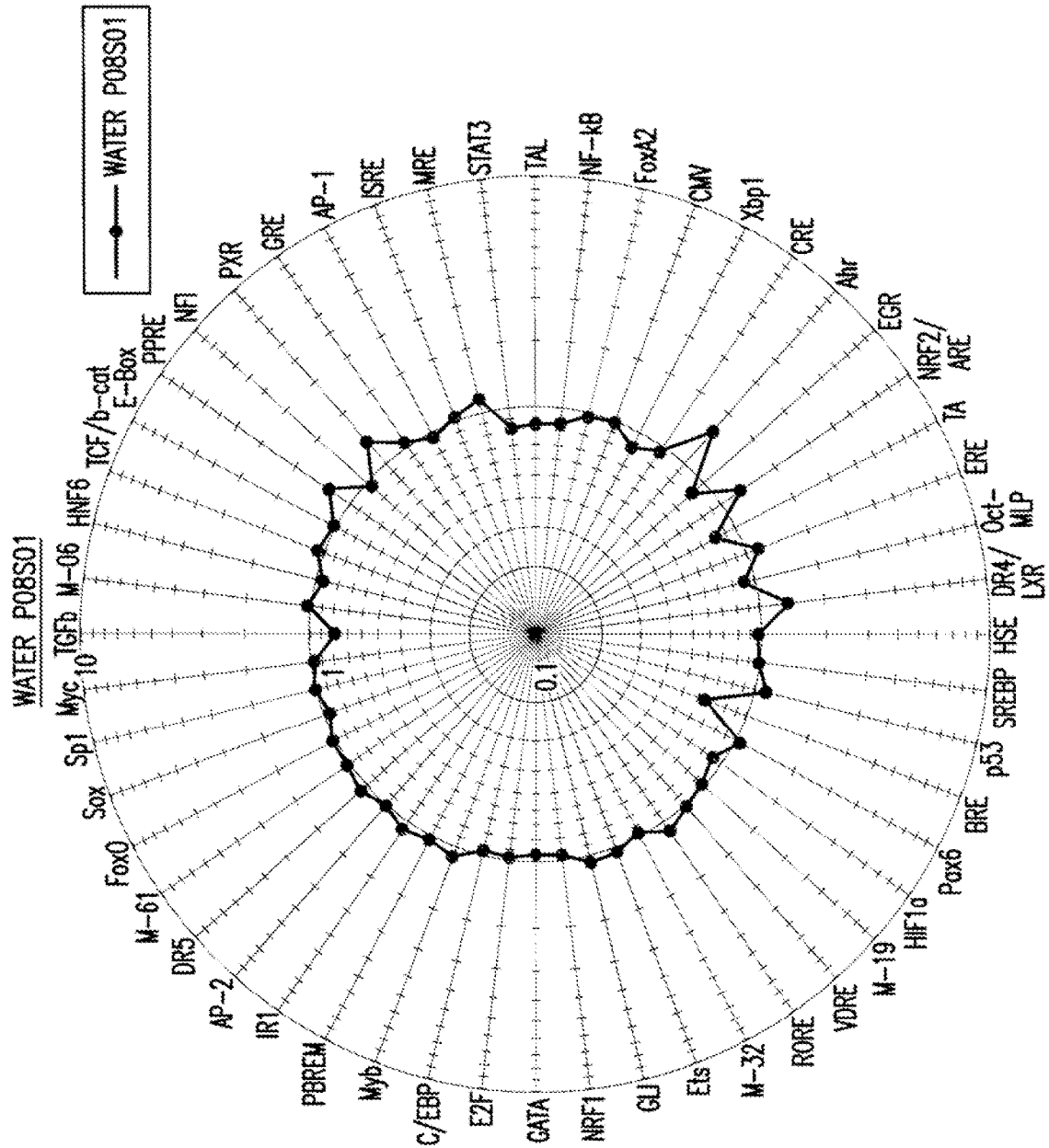

FIGS. 18-22 show tap water quality at selected geographic locations in the United States, in respective transcription factor signatures in the illustrated radar graphs. FIG. 18 shows the transcription factor signature of tap water in Jersey City, N.J. FIG. 19 shows the transcription factor signature of tap water in Laurel, Md., FIG. 20 shows the signature for tap water in Whippany, N.J., FIG. 21 shows the signature of tap water in Fort Lee, N.J., and FIG. 22 shows tap water quality signature in New Orleans, La.

Figure 23:
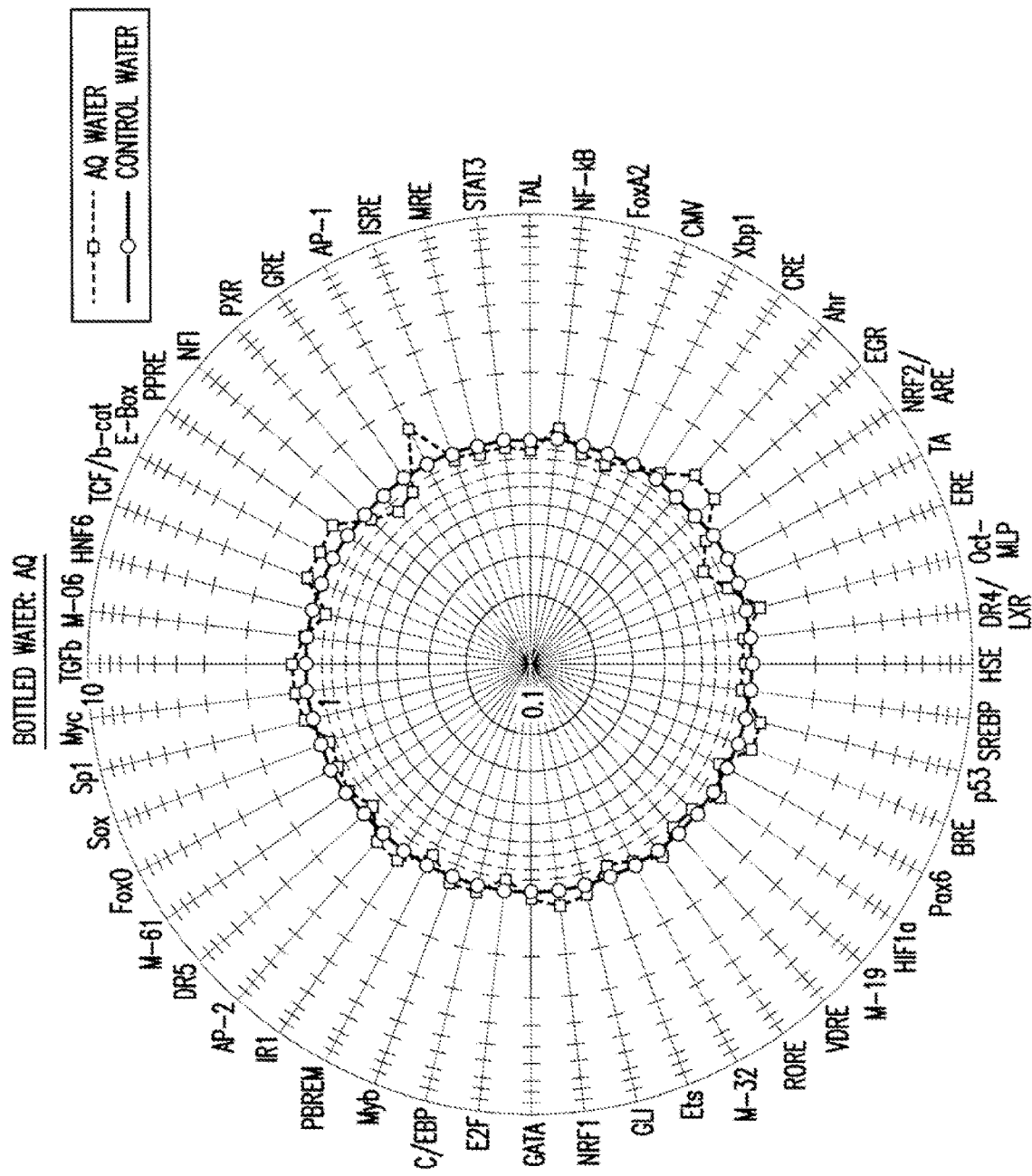
FIGS. 23-26 show transcription factor signatures of evaluated water and control water, for various water sources.
Figure 24:
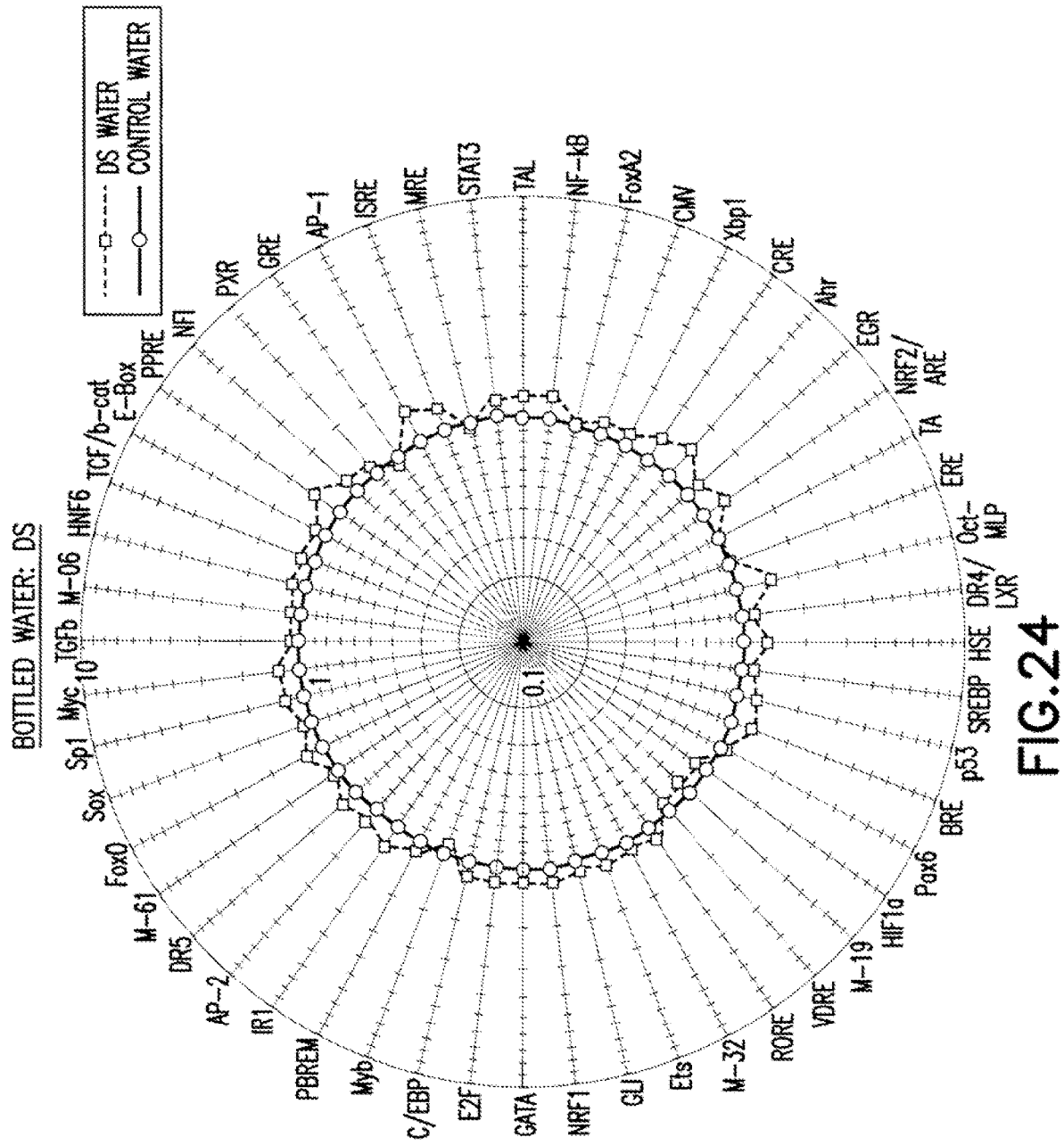
Figure 25:
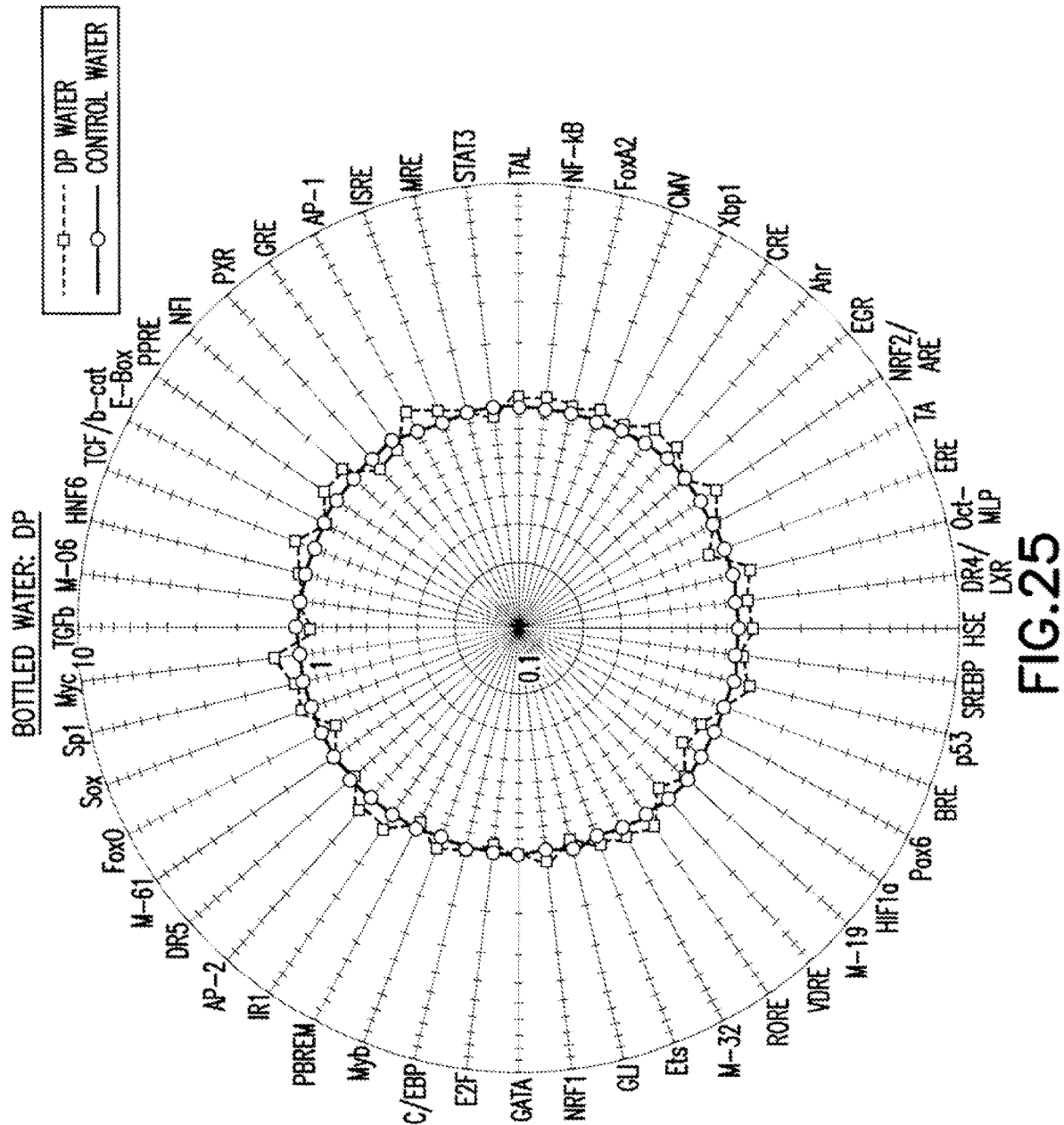
Figure 26:
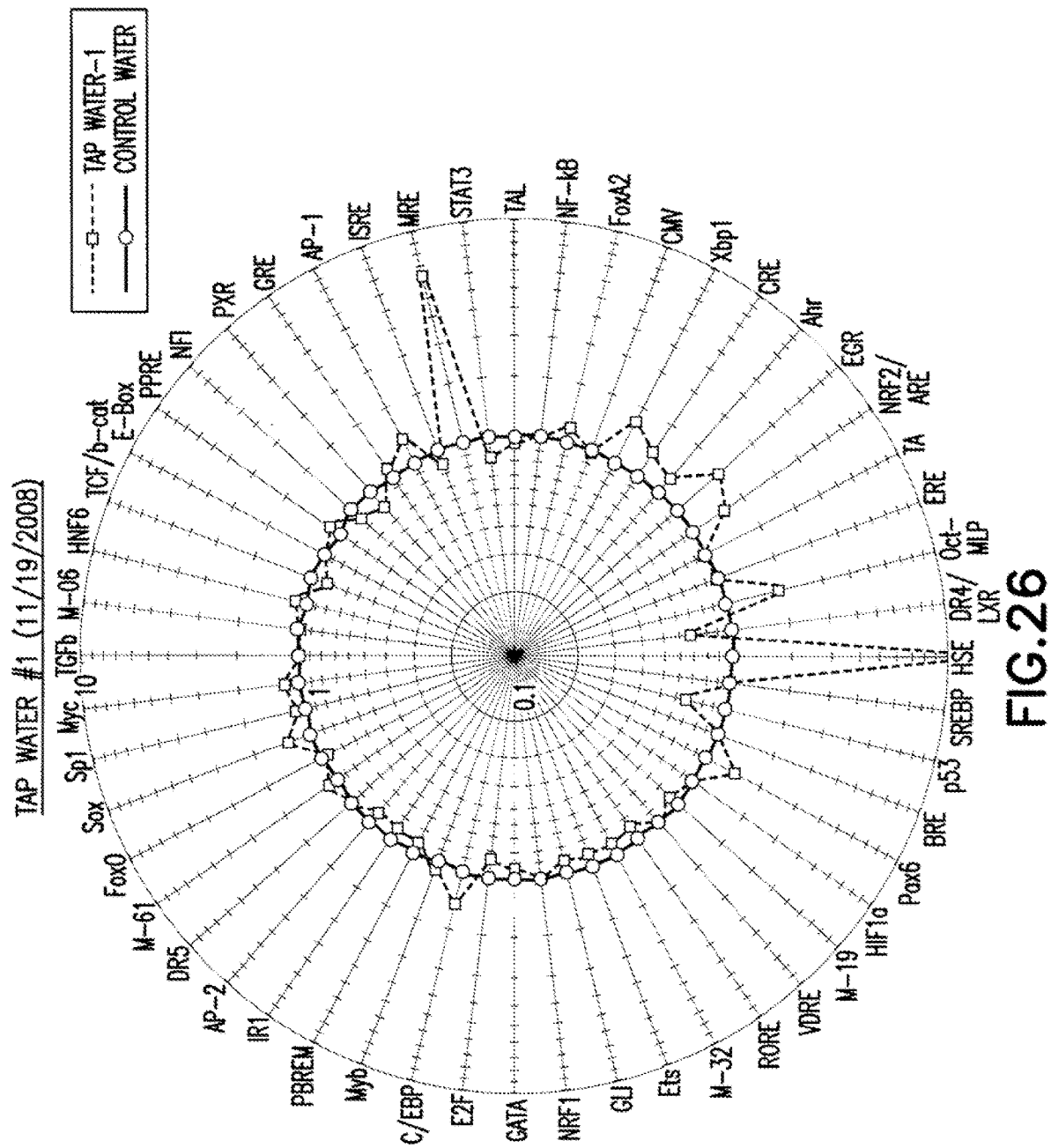

FIGS. 23-26 show transcription factor signatures of evaluated water and control water for various water sources. FIG. 23 shows the transcription factor signature for bottled water (AQ) and control water. FIG. 24 shows corresponding signatures for bottled water (DS) and control water. FIG. 25 shows signatures of bottled water (DP) and control water. FIG. 26 shows signatures of tap water and control water for comparison purposes. Taken together, FIGS. 23-26 provide a comparison of biocontamination levels of three bottled water brands (DP, AQ, DS) and a tap water sample. The data show that water biocontamination levels comparatively were as follows: DP<AQ<DS<<TAP. Accordingly, the bottled waters exhibit significantly better quality than tap water.

The foregoing show that biocontamination levels of drinking water samples can be readily assessed by evaluating a sum of stress responses induced by the evaluated samples in a test cell system, such as the human liver cell line (HepG2) utilizing the biosensor system and methodology of the present disclosure. Biocontamination levels can be assessed regardless of chemical or biological composition of contaminates, and the type of stress-responses indicate probable deleterious effects Tap water samples collected at different time points elicited distinct patterns of stress responses in the cellular assay, indicative of variations of biocontaminants over time. Some tap water samples inhibited key tumor suppressors (e.g. p53), suggesting carcinogenic propensities. Bottled water, in general, induced substantially weaker stress responses than tap water, consistent with significantly reduced levels of biocontamination in bottled water as compared to tap water, in the illustrative samples discussed herein.

The methodology of the present disclosure can be implemented in a variety of water assay system arrangements. For example, a centralized water assay facility can be established, which receives regular samples of water to be evaluated, from a variety of geographic locations, industrial plants or other source group population, and/or assay operations that are of longitudinal temporal character, so that progressions of biocontamination in specific water sources (e.g., lakes, rivers, etc.) can be monitored as a function of time, in support of legislated environmental water quality standards, or to monitor water quality under comparative or other assessment conditions.

The disclosure also contemplates the provision of water quality test kits, that may be utilized for field collection of water samples and performance of assays or assay component activities, as coordinated with a central water quality monitoring facility adapted to produce transcription factor signatures, or other output reports or information reflecting the water samples locally collected for assessment.

Kits may include transcription factor signatures for specific water standards to enable ready visual determination of whether or not biocontamination is or may be present in a particular sample for which a transcription factor signature is generated.

It will be recognized that the apparatus and methodology of the present disclosure enable the quantitative determination of biocontamination water in a simple, effective and accurate manner.

Various aspects of the disclosure are further described below, in specific implementations and embodiments, as contemplated by the disclosure.

In one aspect the disclosure relates to method of determining water quality of a water sample, comprising:

exposing the water sample to a test cell system so that the test cell system responds to the water sample by change in transcription factor activity in said test cell system;

generating from the test cell system response an output correlative to the change of transcription factor activity in said test cell system; and determining from comparison of said output with a transcription factor activity reference standard the quality of the water sample.

Such method may be conducted with the output being one or more profile(s) correlative to the change of transcription factor activity, e.g., a quantitative measure of the cumulative impact on transcription factor activity of cells of a test cell system. The operation of determining the quality of the water sample in such method may include use of a transcription factor activity reference standard that has been generated for a calibration water sample of specific character, e.g., purity, age, historical significance, geolocational attribute, etc. For example, the standard water sample may be a sample that is taken at a specific time and/or location in a longitudinal study to monitor progressionary degradation or improvement of water samples taken at different times and/or locations. The water sample may be a triple distilled deionized water sample.

In the transcription factor activity reference standard, and the output correlative of transcription factor activity in the sample of interest, the reference standard and the output may include profiles as described elsewhere herein, in which the transcription factor peaks in the output spectrum of the capillary electrophoresis plot or the polar coordinate radar graph may be weighted in a cumulated manner to generate the respective profiles.

In such method, a transcription factor signature may be generated for each of said generated profiles, by constructing a library of reporter transcription units (RTUs), in which each RTU is constructed to include a common plasmid backbone and a unique transcription factor-inducible promoter that is fused to a transcribed reporter sequence, and transfecting the library of RTUs into cells of the test cell system.

The transfected library of RTUs in such method produce reporter RNAs in amounts that are commensurate with the activities of the corresponding transcription factors present in the cells of the test cell system. All RTUs are supplied with essentially identical reporter sequences. Each reporter sequence is tagged with a processing tag comprising a restriction cleavage site, the position of which varies among the RTUs.

The above-described method may be carried out, wherein said generating said at least one profile comprises cleaving the restriction cleavage site to yield cleaved reporter species. The cleaved reporter species can then be resolved by capillary electrophoresis. In such method, the cleaved reporter species are advantageously fluorescently labeled. The cleaved reporter species in such method can be produced from the reporter RNAs by reverse transcription and cDNA amplification by polymerase chain reaction using common pairs of primers for all reporter species. Following such operations, profiles can be generated in the form of polar coordinate radar graphs. The generated profile resulting from such methodology may then be subjected to spreadsheet analysis.

In the above-described method, at least one of the generated profiles of ensuing changes in activities of transcription factors in said test cell systems in response to said exposing, and determining from the generated at least one profile the water quality of the water specimen, comprises a computer-implemented processing operation. In specific embodiments, both of the generating and determining comprise computer implemented processing operations. The data from the capillary electrophoresis can be processed to algorithmically subtract background fluorescence for sizing of reporter peaks and noise flash reporter peak discrimination. Fluorescence values of individual reporter peaks may be normalized with the sum of signals of all reporter peaks.

In the above-described method, the transcription profiles can comprise profiles of from 1 to 50 transcription factors, e.g., profiles of from 2 to 10 transcription factors.

The method may be carried out wherein respective transcription factor signatures are algorithmically compared in the determining operation, in a computer-implemented determining process. Such method may be carried out wherein said exposing, generating and determining operations are conducted for at least one water specimen and one or more water standards.

In the above-described method, the test cell system can comprise cells selected from the group consisting of individual cells, cell cultures, single-cell organisms, microbial populations, multicellular organisms, biological specimens taken or derived from such organisms, organs, tissue samples, tissue cultures, endogenous cells, exogenously modified cells, synthetic cells, human cells, animal cells, cloned cells, plant cells, blood cells, platelets, cultured cells, biopsied cells, cells fixed with preservatives, cells bound to substrates, nucleated cells, and non-nucleated cells.

In the method, the generating and determining may comprise assessing changes in DNA-binding activities in cell extracts; may comprise use of a gel-shift assay; and may analyze changes in cellular localization of transcription factors.

In the method described hereinabove, the changes in cellular localization of transcription factors may comprise nuclear translocation of transcription factors.

The method herein comprises representing transcription factor activity profiles by vectors with coordinates x1, x2 . . . xN, where xi is the activity of the $i^{th}$ transcription factor, TE, and said determining comprises assessing Euclidian distance between transcription factor activity vectors.

The above-identified method can be conducted over a period of time to determine improvement or deterioration of water quality in water samples taken at different times from a same water source.

In a further aspect the invention relates to a method of determining water quality of a water specimen, comprising quantifying impacts of contaminants in said water specimen on activities with multiple transcription factors in a test cell system.

In another aspect of the invention, a method of determining relative quality of different water samples, comprising:

exposing each different water sample to a corresponding biosensor comprising multiple transcription factors, wherein the corresponding biosensor is adapted to manifest a transcription factor signature in response to the exposure; and comparing transcription factor signatures of the corresponding biosensors, or of their expression products, to determine relative water quality of the different water samples in relation to one another.

In another aspect the present invention relates to a method of determining water quality of a water sample, comprising:

introducing into a test cell system comprising a multiplicity of transcription factors, a plurality of reporter constructs whose promoters are regulated by the transcription factors;

exposing the test cell system to the water sample to induce corresponding changes in activities of said multiplicity of transcription factors; and determining water quality of the water sample from a plurality of reporter transcripts produced by the reporter constructs and/or a plurality of reporter proteins produced by the reporter constructs in response to the changes in activities of said multiplicity of transcription factors upon exposing the test cell system to water sample.

In still another aspect, the invention relates to an apparatus for determining water quality of a water sample, comprising a computer system adapted to carry out an operation of a method as herein described. In such apparatus, the computer system may comprise networked computers. The networked computers can comprise a central server computer and a client computer.

Figure 27:
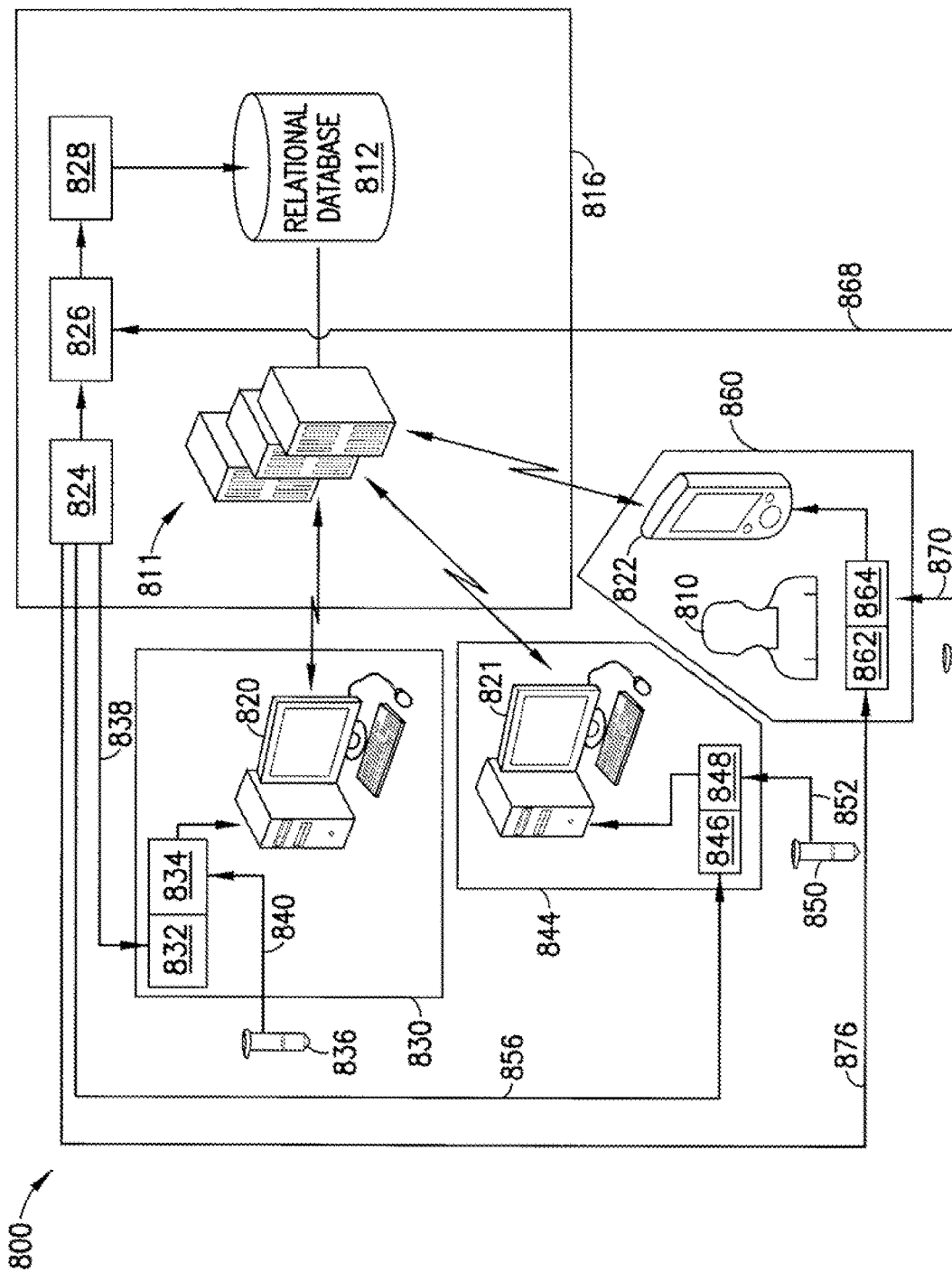
FIG. 27 is a schematic representation of a water quality monitoring system, including a central water quality administration facility, arranged for sample handling and storage, biosensor (test cell) cell culturing, cell plating and processing, database and data analysis, and linked in communication relationship with remote sample input and processing facilities, which may be optionally supplied with reagents, biosensor (test cell) products, and process equipment support from the central facility.

FIG. 27 is a schematic representation of a water quality monitoring system, including a central water quality administration facility, arranged for sample handling and storage, biosensor (test cell) cell culturing, cell plating and processing, database and data analysis, and linked in communication relationship with remote sample input and processing facilities, which may be optionally supplied with reagents, biosensor (test cell) products, and process equipment support from the central facility.

The water quality monitoring system 800 includes a central water quality administration facility 816, in which is disposed a server assembly 811 comprising multiple server units operatively linked to a relational database 812 that may for example contain a library of transcription factor activity reference standards for reference water samples of particular characteristics, as well as protocols for conducting water quality assays using the transcription factor activity methodology of the present disclosure, historical records of longitudinal studies, and other data, accessible to the server units for computational and communicational operations.

The central water quality administration facility 816 also includes a storage inventory of supplies 824, for conducting water quality assays in accordance with the present disclosure, including reverse transcription, PCR, and fluorescent labeling reagents, capillary electrophoresis equipment and supplies, biosensor (test cell) units, cell plating equipment and supplies, computational devices adapted for use at remote sample input and processing facilities, sample collection apparatus, etc.

The central water quality administration facility 816 further includes a water sample processing unit 826 in which a water sample can be contacted with the biosensor (test cells), following which the test cells can be submitted to total RNA isolation, reverse transcription, PCR amplification, fluorescent labeling, restriction digestion, sample clean-up, and capillary electrophoresis. The central facility 816 also includes a primary data analysis unit 828 arranged to receive output from the processing unit 826 and to generate profiles therefore, e.g., for reference samples, or for samples to be assayed as received from a remote sample input and processing facility 860, as hereinafter more fully described.

The system 800 illustratively shown in FIG. 27 includes multiple remote sample input and processing facilities 830, 844, and 860. Each of the remote sample input and processing facilities may be located at substantial distances from the central facility, e.g., in different cites or countries, or even different continents. The remote sample input and processing facilities can be variously constituted, but each is coupled in communication relationship with the central water quality administration facility 816 for bidirectional transmission and receipt of data and signal communications. Such communication coupling may comprise interconnection via a worldwide communication network such as the internet, or other network.

The remote sample input and processing facility 830 is arranged for collection and processing of local water samples 836 that may be introduced to the remote facility as schematically indicated by arrow 840, and assayed in accordance with the transcription factor activity methods of the present disclosure, in processing module 834 which is supplied with equipment and supplies from the supply module 832. The supply module 832 in turn may be supplied from the storage inventory of supplies 824 from the central facility 816, as schematically indicated by arrow 838.

Local water sample assay data generated by the processing module 834 may be transmitted to the central processor unit (CPU) 820 for further processing and transmission to the servers 811 of the central facility 816. The servers 811 then may effect an algorithmic comparison of a transcription factor activity profile for the water sample 836 with a reference standard transcription factor activity profile, and provide resulting comparison data back to the central processor unit (CPU) 820 for local usage at the remote sample input and processing facility 830.

The remote sample input and processing facility 844 is likewise arranged for collection and processing of local water samples 850 that may be introduced to the remote facility as schematically indicated by arrow 852, and assayed in accordance with the transcription factor activity methods of the present disclosure, in processing module 848 which is supplied with equipment and supplies from the supply module 846. The supply module 846 in turn may be supplied from the storage inventory of supplies 824 from the central facility 816, as schematically indicated by arrow 856.

Local water sample assay data generated by the processing module 848 may be transmitted to the central processor unit (CPU) 821 for further processing and transmission to the servers 811 of the central facility 816. The servers 811 then may effect an algorithmic comparison of a transcription factor activity profile for the water sample 850 with a reference standard transcription factor activity profile, and provide resulting comparison data back to the central processor unit (CPU) 821 for local usage at the remote sample input and processing facility 844.

The remote sample input and processing facility 860 includes a supply module 862 that can be supplied with equipment, reagents, and other supplies from the storage inventory of supplies 824 from the central facility 816, as schematically indicated by arrow 876. The supplies from the local supply module 862 are used in processing module 864, which receives local water sample 866, as schematically indicated by arrow 870. In the processing module 864, a local water sample assay is conducted in accordance with the transcription factor activity methodology of the present disclosure, with resulting data being passed to the smartphone 822 of user 810 at the remote facility, and then transmitted to the servers 811 of the central facility, for referential comparison of the transcription factor activity profiles generated at the remote facility 860, to generate a water quality output that is transmitted back to the smartphone, for real-time determinations of the local water quality.

Alternatively, the local water sample 866 can be transmitted directly by the remote facility 860 to the central facility 816, as schematically indicated by arrow 868.

The central facility 816 can also be arranged to provide technical support to the remote facilities, e.g., with updated algorithms, protocols, regulatory updates, etc., as communicated by server units 811 to the remote facilities.

A further aspect of the disclosure relates to a kit for carrying out water quality determination of a water sample, comprising transcription factor signatures for reference library water standards in a graphical format, for threshold visual determinations of relatedness of a transcription factor signature to reference library signatures.

Another aspect of this disclosure relates to a kit for carrying out determinations of water quality of water samples, comprising biosensors, contacting containers in which cells may be contacted with water samples for evaluation, and instructional documents containing protocols for conducting the contacting operation, and the further processing of the contacted cell samples for analysis of transcription factor signatures.

Such kit may comprise one or more of lyzing media, transfection vectors, restriction enzymes, reverse transcription reagents, PCR primers, fluorescent dyes, discs or flash drives containing capillary electrophoresis data processing software, transcription factor signature-generation software, and/or software for conducting other component operations in the water quality determination.

While the disclosure has been set forth herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the invention as hereinafter claimed is intended to be broadly construed and interpreted, as including all such variations, modifications and alternative embodiments, within its spirit and scope.

What is claimed is:

1. A method of identifying water from a remote water source as safe to drink or not, said method comprising:
   (a) obtaining a water sample from the remote water source;
   (b) contacting the water sample with a test cell system comprising a cell transfected with a library of at least 20 reporter transcription units, in which each reporter transcription unit includes a unique transcription factor-inducible promoter and produces a reporter sequence in an amount commensurate with transcription factor activity of a different stress-response pathway of the cell;

(c) conducting an assay of the test cell system to quantify a profile of activity of transcription factors in said different stress-response pathways in the cell of the test cell system;

(d) calculating, in a computer-implemented processing operation conducted at a central facility on a networked computer system including a data structure storing reference transcription factor signatures as a database library of signatures, the contamination of the water sample from the remote water source from said profile of activity of transcription factors as a cumulative index that summarizes the activities of said transcription factors, and algorithmically characterizing the contamination of the water sample from the remote water source in said computer-implemented processing operation against the reference transcription factor signatures of the database library of signatures stored in the data structure of the networked computer system, to generate a computer-implemented processing output of the contamination, comprising a water quality determination of whether water from the remote water source is safe to drink or not; and (e) transmitting the computer-implemented processing output of the contamination, comprising the water quality determination of whether water from the remote water source is safe to drink or not, to a network of the networked computer system whereon it is accessible by a network computer user.

2. The method of claim 1, wherein said test cell system comprises a cell culture of human cells or animal cells.

3. The method of claim 1, wherein said test cell system is a co-culture of different cell types.

4. The method of claim 1, wherein said different stress-response pathways in the cell of the test cell system include the following stress-response pathways: estrogen receptor pathway, pregnane x receptor pathway, ahryloxane receptor pathway, metallothionein response pathway, heat shock response pathway, NF-kappaB pathway, and interferon-specific response pathway.

5. The method of claim 1, wherein said cumulative index summarizes the activity of at least 40 different transcription factors.

6. The method of claim 1, wherein said cumulative index is calculated using fold-induction values.

7. The method of claim 1, wherein said transcription factors comprise transcription factors whose activity is modulated by stress in any of the following stress-response pathways:

estrogen receptor pathway, pregnane x receptor pathway, ahryloxane receptor pathway, metallothionein response pathway, heat shock response pathway, NF-kappaB pathway, interferon-specific response pathway, p53 genotoxic stress response pathway, unfolded protein response pathway, peroxisome proliferator-activated receptor pathway, c-Jun N-terminal kinase pathway, wingless-integrated pathway, transforming growth factor beta pathway, Janus kinase (JAK) signal transducer of activation (STAT) pathway, G-protein coupled receptor (GPCR) pathway, receptor tyrosine kinase pathway, endocrine cell differentiation pathway, osteoblast differentiation pathway, cell proliferation pathway, and lipid homeostasis pathway.

8. The method of claim 1, wherein said cumulative index is a sum of $[\log K_i]^2$, wherein $K_i$ is the activity of transcription factor i.

9. A method of identifying water from a water source as safe to drink or not, said method comprising:

(a) obtaining a water sample from the water source;

(b) contacting the water sample with a test cell system comprising a cell transfected with a library of at least 20 reporter transcription units, in which each reporter transcription unit includes a unique transcription factor-inducible promoter and produces a reporter sequence in an amount commensurate with transcription factor activity of a different stress-response pathway of the cell;

(c) conducting an assay of the test system to quantify a profile of activity of transcription factors in said different stress-response pathways in the cell of the test cell system for the water sample of the water source; and (d) transmitting the activity profile of transcription factors for the water sample of the water source to a central processor unit of a computer system comprising a system memory including a data structure storing reference transcription factor signatures as a database library of transcription signatures, and operating said computer system to algorithmically compare said activity profile of transcription factors against the reference transcription factor signatures of the database library of transcription signatures to generate a corresponding water quality determination that water from the water source is safe to drink or not.

10. The method of claim 9, wherein step (c) is conducted to quantify the profile of the activity of at least 30 different transcription factors.

11. The method of claim 9, wherein said different stress-response pathways in the cell of the test cell system include the following stress-response pathways: estrogen receptor pathway, pregnane x receptor pathway, ahryloxane receptor pathway, metallothionein response pathway, heat shock response pathway, NF-kappaB pathway, and interferon-specific response pathway.

12. The method of claim 9, wherein said transcription factors comprise transcription factors whose activity is modulated by stress in any of the following stress-response pathways:

estrogen receptor pathway, pregnane x receptor pathway, ahryloxane receptor pathway, metallothionein response pathway, heat shock response pathway, NF-kappaB pathway, interferon-specific response pathway, p53 genotoxic stress response pathway, unfolded protein response pathway, peroxisome proliferator-activated receptor pathway, c-Jun N-terminal kinase pathway, wingless-integrated pathway, transforming growth factor beta pathway, Janus kinase (JAK) signal transducer of activation (STAT) pathway, G-protein coupled receptor (GPCR) pathway, receptor tyrosine kinase pathway, endocrine cell differentiation pathway, osteoblast differentiation pathway, cell proliferation pathway, and lipid homeostasis pathway.

13. The method of claim 9, wherein said test cell system comprises HepG2 cells.

14. The method of claim 9, wherein a safe to drink water quality determination corresponds to a predetermined minimum of stress responses being identified by the algorithmic comparison of the activity profile of transcription factors against the reference transcription factor signatures of the database library of transcription signatures.

\* \* \* \* \*

UNITED STATES PATENT AND TRADEMARK OFFICE
CERTIFICATE OF CORRECTION

PATENT NO. : 11,702,707 B2
APPLICATION NO. : 14/343846
DATED : July 18, 2023
INVENTOR(S) : Makarov et al.

It is certified that error appears in the above-identified patent and that said Letters Patent is hereby corrected as shown below:

In the Specification

Column 3, Line 51, "therefore" should be -- therefor --.

Column 17, Line 66, "TE" should be -- TF --.

Column 19, Line 13, "therefore" should be -- therefor --.

Signed and Sealed this
Nineteenth Day of September, 2023

Katherine Kelly Vidal
*Director of the United States Patent and Trademark Office*